(12) United States Patent
Itamochi et al.

(10) Patent No.: US 12,420,283 B2
(45) Date of Patent: Sep. 23, 2025

(54) SPECIMEN-PRESERVING IMPLEMENT

(71) Applicant: Kao Corporation, Tokyo (JP)

(72) Inventors: Shinya Itamochi, Odawara (JP);
Masahiro Oka, Sumida-ku (JP);
Shuhei Matsumoto, Odawara (JP);
Takenori Shiraiwa, Odawara (JP)

(73) Assignee: Kao Corporation, Tokyo (JP)

( * ) Notice: Subject to any disclaimer, the term of this patent is extended or adjusted under 35 U.S.C. 154(b) by 186 days.

(21) Appl. No.: 18/043,212

(22) PCT Filed: Aug. 27, 2021

(86) PCT No.: PCT/JP2021/031588
§ 371 (c)(1),
(2) Date: Feb. 27, 2023

(87) PCT Pub. No.: WO2022/045309
PCT Pub. Date: Mar. 3, 2022

(65) Prior Publication Data
US 2023/0364617 A1    Nov. 16, 2023

(30) Foreign Application Priority Data

Aug. 28, 2020 (JP) ................................ 2020-144698

(51) Int. Cl.
*B01L 3/00* (2006.01)
*B65D 51/30* (2006.01)
(Continued)

(52) U.S. Cl.
CPC .............. *B01L 3/508* (2013.01); *B65D 51/30* (2013.01); *B65D 81/18* (2013.01); *B65D 81/266* (2013.01);
(Continued)

(58) Field of Classification Search
CPC ...... B65D 51/30; B65D 81/18; B65D 81/266; B01L 3/508; B01L 2200/0689; B01L 2300/042; B01L 2300/105; A61B 10/0096
See application file for complete search history.

(56) References Cited

U.S. PATENT DOCUMENTS

| 5,505,308 A | * | 4/1996 | Eikmeier | ............... B65D 43/26 |
| | | | | 206/569 |
| 5,788,064 A | * | 8/1998 | Sacherer | ............... B65D 53/00 |
| | | | | 220/849 |

(Continued)

FOREIGN PATENT DOCUMENTS

| JP | 2014-010132 A | 1/2014 |
| JP | 2014-515108 A | 6/2014 |

(Continued)

OTHER PUBLICATIONS

U.S. Appl. No. 18/043,254, filed Feb. 27, 2023, Nagamori, Natsumi et al.

(Continued)

*Primary Examiner* — Chun Hoi Cheung
(74) *Attorney, Agent, or Firm* — Oblon, McClelland, Maier &Neustadt, L.L.P.

(57) ABSTRACT

A specimen-preserving implement including, a medium-containing section capable of accommodating a medium holding a specimen, a degradation inhibitor in liquid form that inhibits degradation of a sample to be tested contained in the specimen, an agent holder capable of being impregnated with the degradation inhibitor, and a containing section of a desiccant. The degradation inhibitor transfers to the medium by placing the medium in the medium-containing section in a state in which the agent holder is impregnated with the degradation inhibitor, and the desiccant is enabled to absorb humidity released from the degradation inhibitor (Continued)

without directly contacting the agent holder in a state in which the medium is accommodated in the medium-containing section.

18 Claims, 13 Drawing Sheets

(51) Int. Cl.
    *B65D 81/18* (2006.01)
    *B65D 81/26* (2006.01)

(52) U.S. Cl.
    CPC . *B01L 2200/0689* (2013.01); *B01L 2300/042* (2013.01); *B01L 2300/105* (2013.01)

(56) References Cited

U.S. PATENT DOCUMENTS

| | | | |
|---|---|---|---|
| 6,231,815 B1* | 5/2001 | Bainczyk | B01L 3/5023 422/550 |
| 6,539,817 B2* | 4/2003 | Kozak | B01L 3/5029 422/550 |
| 6,705,463 B1* | 3/2004 | Bucholtz | B65D 43/162 206/315.9 |
| 7,537,137 B2* | 5/2009 | Giraud | B65D 53/00 220/4.23 |
| 8,236,254 B2* | 8/2012 | Myles | B01L 3/508 312/294 |
| 8,388,905 B2* | 3/2013 | Neel | G01N 33/48757 221/65 |
| 8,394,343 B2* | 3/2013 | Chan | G01N 33/48778 422/68.1 |
| 9,370,775 B2* | 6/2016 | Harvey | G01N 1/02 |
| D892,310 S | 8/2020 | Jordan et al. | |
| D949,329 S | 4/2022 | Jordan et al. | |
| 11,325,129 B2* | 5/2022 | Staton | B65D 1/36 |
| 2004/0116826 A1 | 6/2004 | Jung et al. | |
| 2009/0216213 A1 | 8/2009 | Muir et al. | |
| 2010/0000905 A1* | 1/2010 | Wang | B65D 83/02 206/569 |
| 2010/0140116 A1* | 6/2010 | Stiene | B65D 81/266 206/459.1 |
| 2010/0209957 A1 | 8/2010 | Hogan et al. | |
| 2011/0247949 A1* | 10/2011 | Yao | B65D 43/162 53/471 |
| 2013/0334074 A1* | 12/2013 | Wada | B65D 81/266 206/204 |
| 2014/0000392 A1 | 1/2014 | Harvey et al. | |
| 2014/0038172 A1* | 2/2014 | De La Rosa | C12N 1/04 435/5 |
| 2016/0024559 A1 | 1/2016 | Sangha et al. | |
| 2016/0263577 A1 | 9/2016 | Ismagilov et al. | |
| 2018/0299354 A1 | 10/2018 | Mao et al. | |
| 2018/0371524 A1 | 12/2018 | Inoue et al. | |
| 2019/0000365 A1 | 1/2019 | Beyerlein et al. | |
| 2020/0163603 A1 | 5/2020 | Jordan et al. | |
| 2020/0164359 A1 | 5/2020 | Jordan et al. | |
| 2020/0164362 A1 | 5/2020 | Jordan et al. | |
| 2022/0361784 A1 | 11/2022 | Jordan et al. | |
| 2023/0258539 A1* | 8/2023 | Johnson | G01N 1/10 422/527 |

FOREIGN PATENT DOCUMENTS

| | | |
|---|---|---|
| JP | 2015-525890 A | 9/2015 |
| JP | 2022-040103 A | 3/2022 |
| WO | WO 2015/044227 A1 | 4/2015 |
| WO | WO 2017/210218 A1 | 12/2017 |

OTHER PUBLICATIONS

International Search Report mailed on Oct. 26, 2021 in PCT/JP2021/031588 filed on Aug. 27, 2021 (3 pages).
Extended European Search Report issued Sep. 16, 2024 in European Patent Application No. 21861730.6, 8 pages.

* cited by examiner (a)

(b)

(a)

(b)

(a)

(b)

SPECIMEN-PRESERVING IMPLEMENT

CROSS REFERENCE TO RELATED APPLICATIONS

This application is a National Stage entry under 35 U.S.C. § 371 of PCT/JP2021/031588, filed on Aug. 27, 2021, and claims priority to Japanese Patent Application No. 2020-144698, filed on Aug. 28, 2020. The entire contents of both are incorporated herein by reference.

TECHNICAL FIELD

The present invention relates to a specimen-preserving implement.

BACKGROUND ART

Nucleic acids contained in specimens collected from living organisms are analyzed and used for various diagnoses. For example, methods for collecting specimens containing nucleic acids from a living organism include a method for collecting mucosal cells from tissues in an oral cavity, a method for collecting blood by pricking with an injection needle, a method for collecting cells from tissues in a body or the like, and as less invasive methods, there are methods which use saliva, hair or the like.

Further, the present applicant finds that RNA derived from an individual exists in skin surface lipids and reports a method for preparing nucleic acids derived from skin cells of a subject including separation of the nucleic acids from the skin surface lipids collected from the subject based on the finding (Patent Literature 1).

If it takes time from collection of a specimen to analysis of the specimen, it is necessary to store the collected specimen in a state in which degradation of nucleic acids is inhibited. As a method for storing the specimen, there are known a method for storing a specimen at a low temperature of minus 80° C., and a method of using a preservation solution, for example. The method for storing a specimen at a low temperature requires a large amount of money for equipment that maintains the low temperature, and if transportation is required from a specimen collection site to a specimen analysis site, a device that transports the specimen while maintaining the low temperature is required.

As the method of using a preservation solution, there are a method of directly putting a medium holding a specimen into a container in which the preservation solution is stored, and a method of dropping a preservation solution directly onto a medium holding a specimen. The method of using a preservation solution can simplify equipment and devices as compared with the method of storing a specimen at a low temperature, but there is a risk that the preservation solution may spill or scatter around. Further, when a preservation solution having properties that are undesirable when it contacts a body is used as the preservation solution, it is further necessary to devise a way to collect the specimen so that the preservation solution does not contact the body.

As a technique for collecting a specimen so that the preservation solution does not contact a body, as a technique of using saliva as a specimen, there is proposed a container system in which a penetration member provided at a lid penetrates a partition membrane between a collection portion and a preservation solution by closing the lid after the saliva is collected into the funnel-shaped collection portion, and the saliva and the preservation solution are mixed (Patent Literature 2).

CITATION LIST

Patent Literature

Patent Literature 1: US 2018371524 A1
Patent Literature 2: US 2009216213 A1

SUMMARY OF INVENTION

The present invention relates to a specimen-preserving implement including: a medium-containing section in which a medium holding a specimen is accommodated; a degradation inhibitor in liquid form that inhibits degradation of a sample to be tested contained in the specimen; an agent holder capable of being impregnated with the degradation inhibitor; and a containing section of a desiccant. The degradation inhibitor transfers to the medium by placing the medium in the medium-containing section in a state in which the agent holder is impregnated with the degradation inhibitor, and the desiccant is enabled to absorb humidity released from the degradation inhibitor without directly contacting the agent holder, in a state in which the medium is accommodated in the medium-containing section.

DESCRIPTION OF EMBODIMENTS

In the container system of Patent Literature 2, the preservation solution is used as a liquid.

When the medium in which a specimen is collected is stored in a preservation solution, if the preservation solution is an aqueous solution, for example, there may be cases that are not preferable as a storage environment for the specimen, such as cases in which the specimen or a component to be tested in the specimen may be removed from the medium, and in which the specimen or the component to be tested in the specimen may be easily degraded by hydrolysis due to moisture in the preservation solution depending on the type of the component to be tested in the specimen.

The present invention relates to a specimen-preserving implement that can solve the problem to be solved of the conventional arts.

Hereinafter, the present invention is described based on preferable embodiments of the present invention with reference to the drawings.

Figure 1:
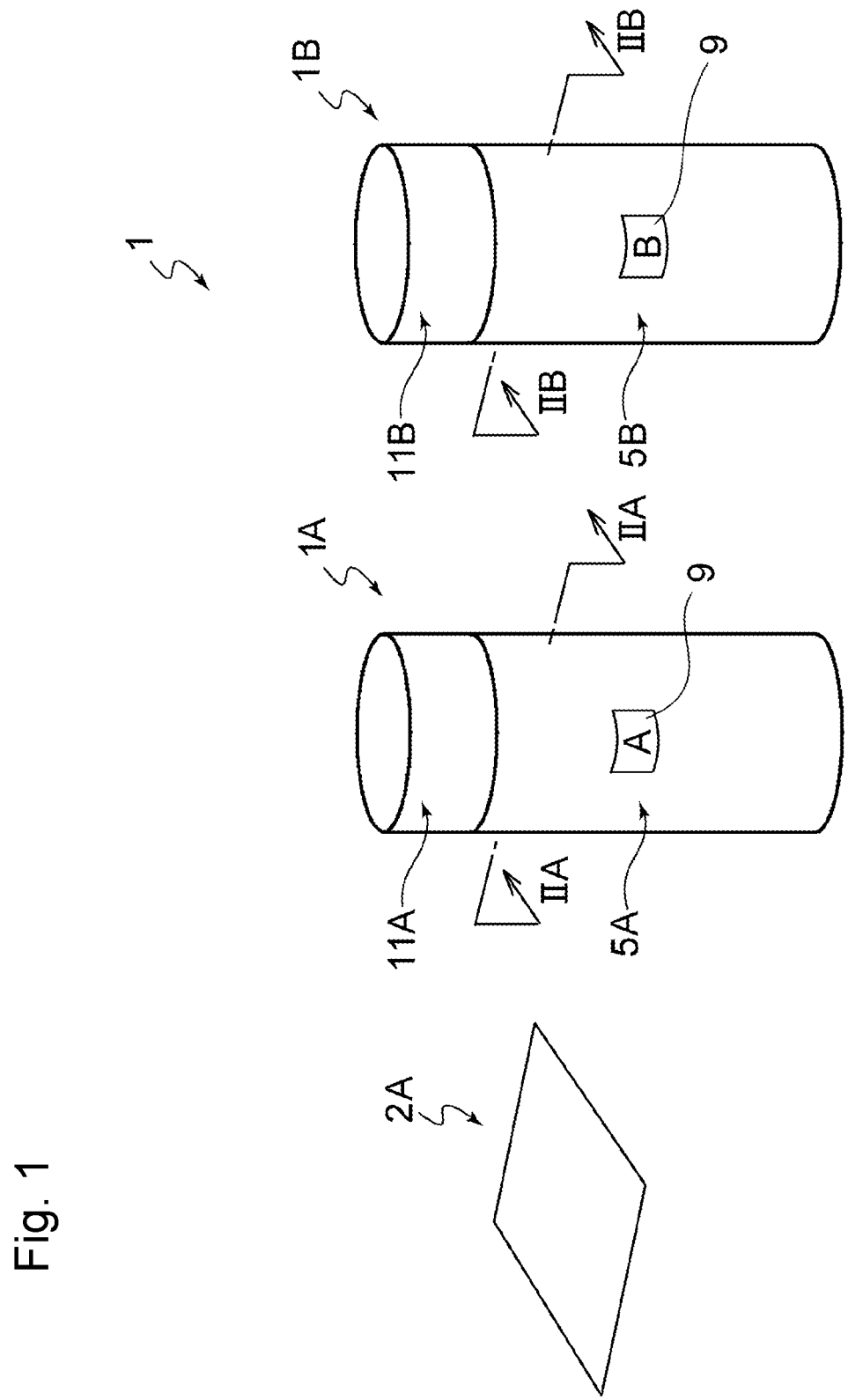
FIG. 1 is a perspective view showing a specimen-preserving implement of a first embodiment of the present invention.
Figure 2:
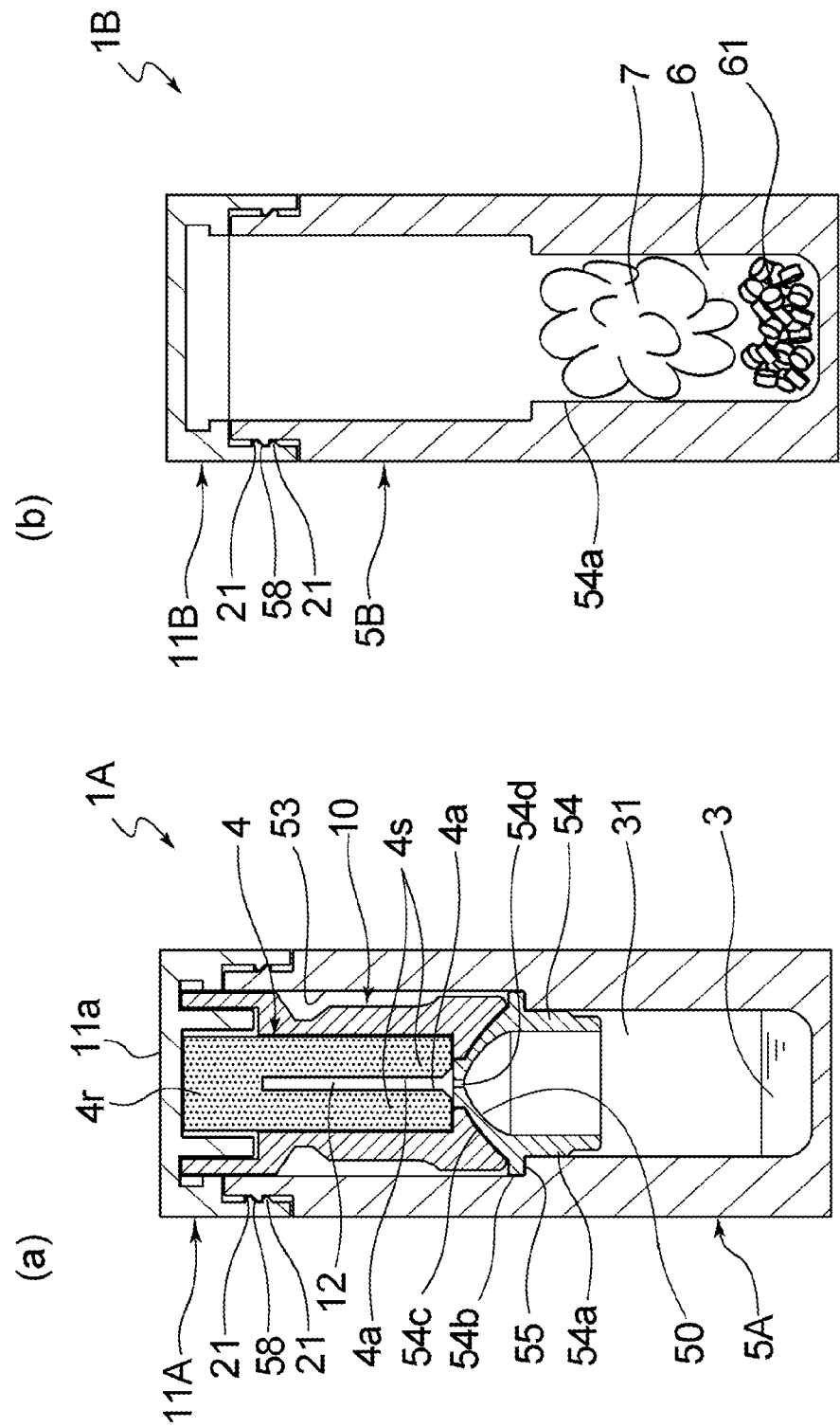
FIG. 2 (a) and FIG. 2 (b) are sectional views each showing a specimen-preserving implement according to the first embodiment of the present invention, FIG. 2 (a) is a sectional view taken along line IIA-IIA of a first container shown in FIG. 1, and FIG. 2 (b) is a sectional view taken along line IIB-IIB of a second container shown in FIG. 1.

FIG. 1 and FIG. 2 are views showing a specimen-preserving implement 1 according to a first embodiment of the present invention.

As shown in FIG. 2, the specimen-preserving implement 1 of the first embodiment includes a first container 1A and a second container 1B, has a medium-inserted portion 12 as a medium-containing section in which a medium 2 holding a specimen is accommodated, a liquid degradation inhibitor 3 that inhibits degradation of a sample to be tested contained in the medium, and an agent holder 4 capable of being impregnated with the degradation inhibitor 3 in the first container 1A, and has a containing section 6 of a desiccant in the second container 1B.

FIG. 2 shows a state before the medium 2 holding the specimen is accommodated in the medium-inserted portion 12. The specimen-preserving implement 1 is preferably provided to a user of a specimen-preserving implement, or distributed, with the first container 1A and the second container 1B as a set, more preferably, as a set including a medium 2A capable of holding a specimen in addition to the set of the first container 1A and the second container 1B. The user of the specimen-preserving implement is a person who performs an operation of accommodating the medium 2 holding a specimen into the medium-containing section of the specimen-preserving implement 1, and bringing the medium 2 into a state of being stored in the specimen-preserving implement 1, and may be a researcher, a general consumer or the like without being limited to medical personnel such as a doctor and a nurse. The specimen-preserving implement of the present invention has such convenience that even a general consumer can handle it with peace of mind. The first container 1A and the second container 1B preferably have identification representations 9 that make both of them easily discriminable. The identification representation 9 is provided by any method such as labelling and printing.

The medium 2 holding a specimen is accommodated in the medium-inserted portion (medium-containing section) 12. The medium 2 holding a specimen is a medium obtained by causing the medium 2A capable of holding a specimen to hold the specimen by an arbitrary method. The specimen that is held by the medium 2A is preferably a specimen derived from an animal, and preferably contains nucleic acids, proteins, metabolites, and the like as a sample to be tested. The animal mentioned here includes mammals including humans and non-human mammals, birds, reptiles, amphibians, fish, insects and the like.

As the specimens derived from animals, for example, skin surface lipids, saliva, blood, bodily fluids and the like are cited, for example. A subject from which the specimen is collected may be any of a living body of a living animal, a dead animal, and a non-living organism to which a specimen derived from an animal is attached, but is preferably a living organism from a viewpoint of use in diagnosis and prediction of health conditions of various living organisms.

Skin surface lipids refer to fat-soluble fractions present on a surface of a skin, and are also referred to as sebum. Hereinafter, skin surface lipids are also referred to as "sebum". In general, sebum mainly contains secretions secreted from exocrine glands such as sebaceous glands on a skin surface, and is present on a skin surface in a form of a thin layer covering the skin surface. Unless otherwise specified, a skin is a general term for areas including tissues such as epidermis, dermis, hair follicles, sweat glands, sebaceous glands and other glands on a body surface.

The present applicant reports that sebum contains nucleic acids, in particular, RNA derived from cells of a subject from which the sebum is collected (see Patent Literature 1). Accordingly, a typical example of a sample to be tested when the specimen is sebum is nucleic acids. It is preferable to use sebum as a specimen and store the sebum in the specimen-preserving implement of the present invention so that nucleic acids are not degraded, from a viewpoint of being able to collect a specimen containing nucleic acids from a living subject easily and less invasively, and a viewpoint of being able to inhibit degradation of nucleic acids and perform various analyses or analytical studies effectively, even if an amount of the nucleic acids contained in the sebum is comparatively small.

A method for analysis or analytic study of the nucleic acids in the specimen after being stored is not particularly limited, and various known methods or the like can be used, and can be properly determined according to a purpose of the analysis or analytical study. As a method for separating nucleic acids from the specimen after being stored in the specimen-preserving implement, various known methods can be used.

The sebum collected from a subject contains nucleic acids expressed in skin cells of the subject, preferably contains nucleic acids expressed in any of an epidermis, sebaceous glands, hair follicle, sweat glands, and dermis of the subject, and more preferably contains nucleic acids expressed in any of the epidermis, sebaceous glands, hair follicle, and sweat glands of the subject. The nucleic acids prepared from the specimen after being stored in the specimen-preserving implement and derived from the skin cells of the subject are preferably nucleic acids derived from at least one site selected from epidermis, sebaceous glands, hair follicle, sweat glands and dermis of the subject, and more preferably nucleic acids derived from at least one site selected from epidermis, sebaceous glands, hair follicle, and sweat glands.

The nucleic acids derived from sebum collected from a subject are useful as a sample for gene expression analysis study concerning a skin of a subject from which sebum epidermis lipids are collected and analytical study on other gene information, function analysis study concerning the skin of the subject, analytical study on a skin condition of the subject (for example, diagnosis of dermatitis), analytical study on sites other than the skin of the subject or a whole body condition (for example, diagnosis of various diseases) and the like. As a method for analysis or analytical study of nucleic acids obtained from sebum, various methods described in Patent Literature 1 can be used, for example.

In the present invention, the nucleic acid that is a component to be tested may be either DNA or RNA and is preferably RNA. As RNA, there are cited mRNA, tRNA, rRNA, small RNA (for example, microRNA (miRNA), small interfering RNA (siRNA), Piwi-interacting RNA (piRNA) and the like), long intergenic non-coding (linc) RNA and the like. mRNA is RNA that encodes protein, and many have a length of 1000 nt or more. miRNA, siRNA, piRNA and lincRNA are non-coding (nc) RNA that does not encode protein. miRNA is RNA that is small and has a length of about 19 to 30 nt, of nc RNA. LincRNA is long non-coding RNA having poly-A similarly to mRNA, and has a length of 200 nt or more. When the specimen is sebum, the nucleic acid as a component to be tested contained in the specimen is preferably RNA having a length of 200 nt or more, and more preferably is at least one kind selected from a group including mRNA and lincRNA.

The specimen-preserving implement 1 of the first embodiment is further described.

As shown in FIG. 1 and FIG. 2 (*a*), the first container 1A has a cap section 11A and a container body 5A to which the cap section 11A is fitted. The cap section 11A is detachably and attachably fitted to one end opening of the container body 5 in a bottomed cylindrical shape.

The first container 1A has the medium-inserted portion 12, the liquid degradation inhibitor 3 and the agent holder 4. The agent holder 4 is held by the cap section 11A of the first container 1A, and even when the cap section 11A is detached from the container body 5A, a state of being held by the cap section 11A is maintained (see FIG. 3). The liquid degradation inhibitor 3 is accommodated in a storage 31 for a degradation inhibitor that is provided in the container body 5A.

The agent holder 4 can be impregnated with the liquid degradation inhibitor 3 and can maintain an impregnated state. A forming material of the agent holder 4 is preferably a material that holds a liquid among fibers (or pores) but does not absorb a liquid (moisture) into a material (fiber) itself, from a viewpoint of making holdability of the liquid degradation inhibitor 3 and transferability of the liquid to the medium good. As examples of the preferable forming material of the agent holder 4, porous and soft materials are cited, and for example, felt, sponge, nonwoven fabric or the like, or a laminate or the like of one kind or two kinds or more of these materials is cited.

The forming material of the agent holder 4 may be wool, wood pulp and the like besides a synthetic resin, and is preferably a material mainly composed of a synthetic resin from a viewpoint of containing no nucleic acids and a viewpoint of drug resistance. A mass proportion of a synthetic resin of the forming material mainly composed of the synthetic resin is preferably 50% or more of a total mass, is preferably 90% or more, and more preferably 100%.

Figure 3:
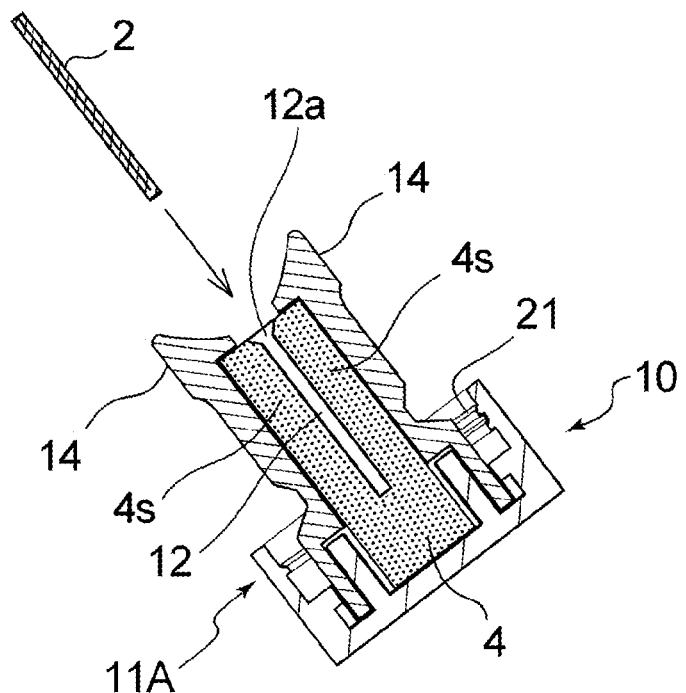
FIG. 3 is a sectional view showing a cap complex detached from the first container.
Figure 4:
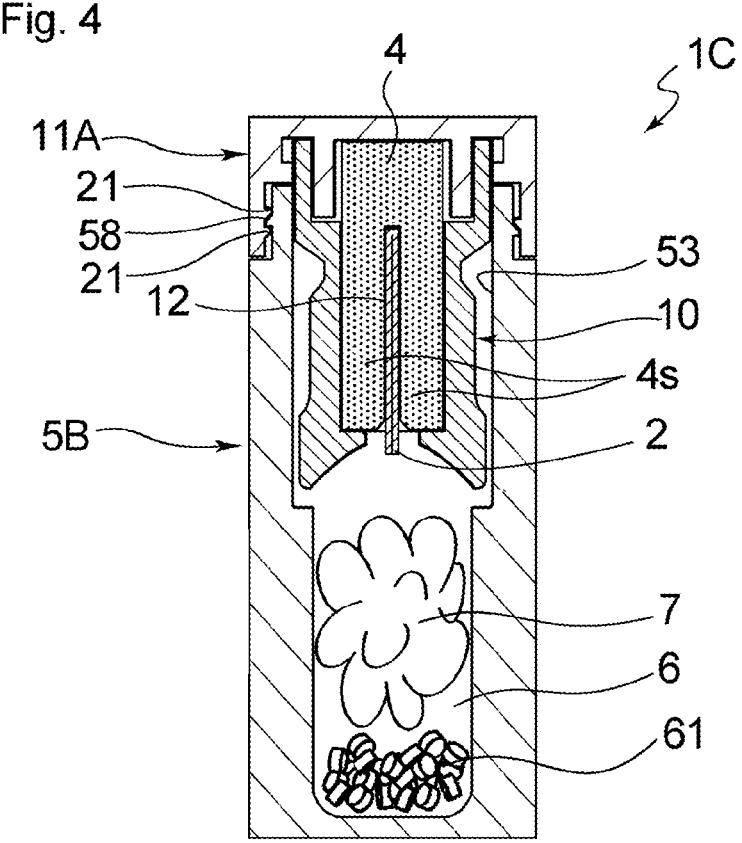
FIG. 4 is a sectional view showing a state in which a cap section of the first container is fitted to a container body of the second container in the first embodiment, and is a view corresponding to FIG. 2 (a).

As shown in FIG. 2 to FIG. 4, the first container 1A in the first embodiment includes the medium-inserted portion 12 where the medium 2 is inserted and the medium 2 is held, as a medium-containing section in which the medium 2 holding a specimen is accommodated, in the agent holder 4. The medium-inserted portion 12 is preferably capable of holding the medium 2 by only inserting the medium 2. Explaining the medium-inserted portion 12 in the present embodiment more specifically, the agent holder 4 includes a pair of agent holding portions 4s and 4s that face each other with the medium-inserted portion 12 therebetween as shown in FIG. 2 (*a*), and when the medium 2 is inserted into the medium-inserted portion 12, the medium 2 receives pressure from the pair of agent holding portions 4s and 4s, and thereby the medium 2 is stably held in the medium-inserted portion 12. The pair of agent holding portions 4s and 4s may be such that two independent agent holders are disposed in a state close to each other or in contact with each other so that the medium-inserted portion 12 is formed therebetween, but in the present embodiment, as shown in FIG. 2 (*a*), a slit-like cut portion is provided in the single agent holder 4, and the agent holder 4 has an undivided portion 4r that connects the agent holding portions 4s and 4s on a top surface section 11a side of the cap section 11A.

Opposing surfaces 4a of the pair of agent holding portions 4s and 4s may contact each other or may not contact each other in a state before the medium 2 is inserted into the medium-inserted portion 12. A distance between the pair of the opposing surfaces 4a can be properly determined in consideration of thickness of the medium 2 at a time of being inserted into the medium-inserted portion 12 and transferability of a degradation inhibitor to the medium 2 from the agent holder 4.

A shape of the medium 2A holding the specimen can be an arbitrary shape such as a sheet-like shape, a block-like shape, or a spherical shape having a handle, but is preferably a sheet-like shape as shown in FIG. 1. The sheet-like medium 2A preferably has flexibility, and is preferably capable of being folded up.

The sheet-like medium 2A is preferable from a viewpoint of collection efficiency and workability when collecting the specimen from a skin of an animal, or from a viewpoint of capable of reducing a form during storage as compared with an area during collection, by being folded up after holding the specimen. Further, when collecting the specimen from a skin of human or non-human animal, use of the sheet-like medium 2A has an advantage that the sheet deforms during collection and can reduce stimulus to the skin. As the sheet-like medium 2A, a porous sheet can also be used. Use of a porous sheet is preferable because the specimen is adsorbed into micropores in the sheet, and the specimen can be held by the sheet more firmly.

The sheet-like medium 2 after holding the specimen is preferably accommodated in the medium-inserted portion 12 in a state where the medium 2 is folded up a plurality of times from a viewpoint of enabling downsizing of the specimen-preserving implement 1 and improving transportability and handleability. The distance between the inner surfaces 4a of the agent holding portions 4s and 4s that oppose each other with the medium-inserted portion 12 therebetween can be properly set from a viewpoint of insertion easiness of the medium 2A and causing the medium 2 to be maintained stably in the medium-inserted portion 12 even if fingers or an instrument contacting the medium 2A are removed at a time of insertion, and is, for example, 0 mm or more and 10 mm or less, and preferably 0 mm or more and 7 mm or less. The distance between the inner surfaces 4a of the pair of agent holding portions 4s and 4s is measured in a natural state before the medium 2 is inserted.

As a method for holding a specimen in the medium 2A, any method that can hold the specimen can be used without particular limitation according to the type of the specimen. For example, as a method for collecting sebum as the specimen, there are cited a method of collecting sebum by causing the medium 2A that can hold the specimen to directly contact a skin, and a method for transferring collected specimen by rubbing the specimen against the medium 2A by using an instrument such as spatula, or a scraper. The medium 2A capable of holding a specimen preferably has high adsorbability for the specimen according to the specimen, and use of a sheet-like specimen adsorbent is more preferable. As a sheet-like specimen adsorbent in the case of the specimen being sebum, a sheet-like material having adsorbability for sebum such as oil blotting paper, and an oil blotting film, for example, can be used. Further, in order to enhance adsorbability of sebum, a sheet-like material containing a solvent having high fat-solubility in advance can also be used. On the other hand, when the sheet-like medium 2A contains a highly water-soluble solvent or moisture, adsorption of sebum is suppressed, and therefore the sheet-like medium 2A is preferably used in a dry state.

Figure 5:
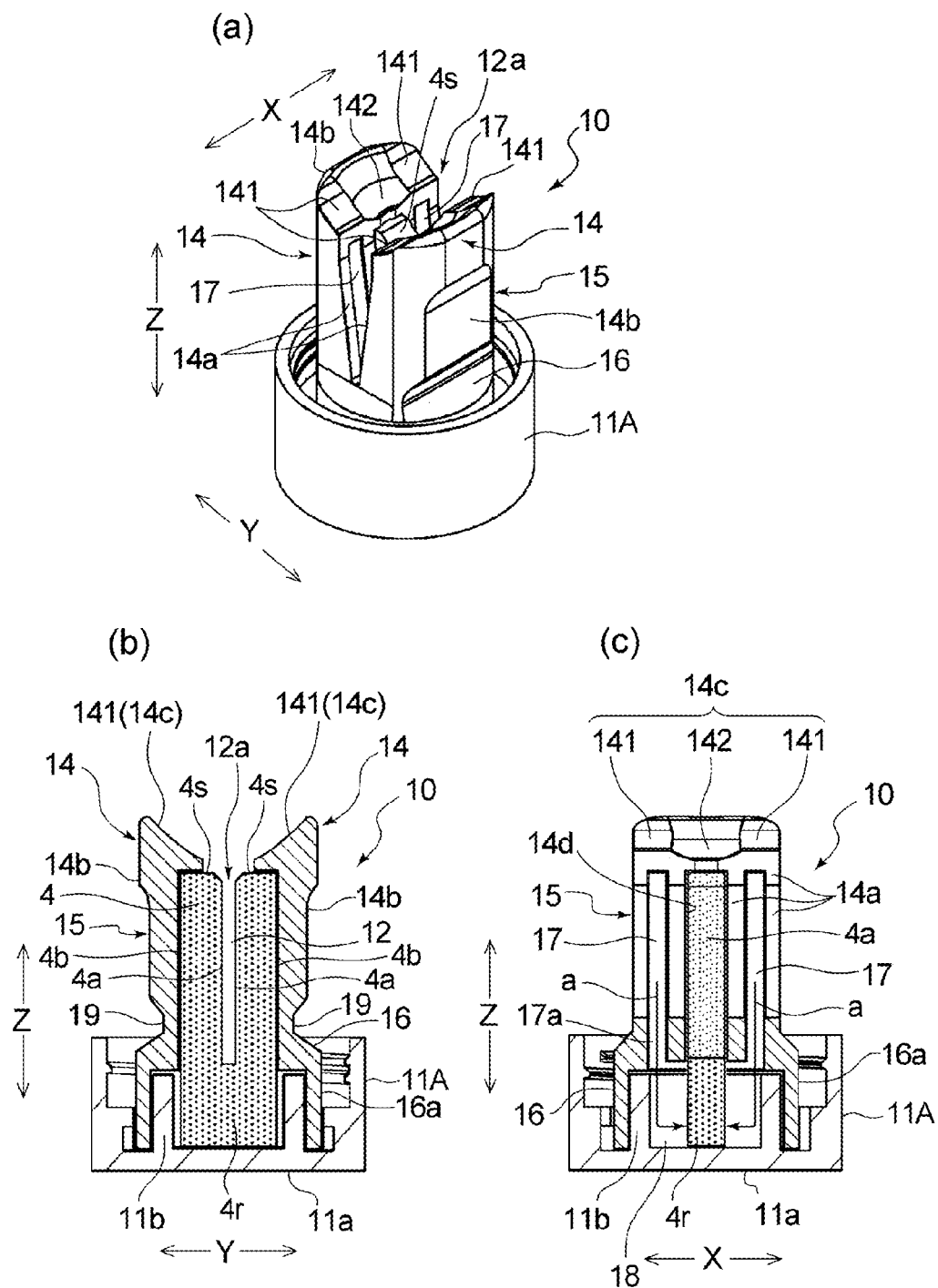
FIG. 5 (a) to FIG. 5 (c) are views showing a cap complex detached from the first container, FIG. 5 (a) is a perspective view, FIG. 5 (b) is a sectional view along a second direction Y, and FIG. 5 (c) is a sectional view along a first direction X.

As shown in FIG. 5 (b), the first container 1A of the present embodiment incudes a pair of outside support portions 14 that cover outer surface 4b sides of the agent holder 4 on both sides of the medium-inserted portion 12.

Explaining more specifically, the first container 1A includes a support portion forming member 15 connected to the cap section 11A. The support portion forming member 15 is a member that supports the agent holder 4 in a state of being held by the cap section 11A, and a part of the member forms the pair of outside support portions 14. The cap section 11A, the agent holder 4 and the support portion forming member 15 form the cap section complex 10 that can be handled integrally with the cap section 11A when the cap section 11A is detached from the container body 5A.

The support portion forming member 15 includes a base portion 16 located on a side of a connection portion with the cap section 11A, and the pair of outside support portions 14 and 14 that extend to branch into two toward a tip end side in a direction to protrude from the cap section 11A. The base portion 16 of the support portion forming member 15 is fixed to the cap section 11A. Specifically, a tubular connection portion 16a formed at a lower part of the base portion 16 is fitted onto a tubular connection portion 11b formed on an inner surface side of the top surface section 11a of the cap section 11A, and thereby is fixed to the cap section 11A.

Figure 6:
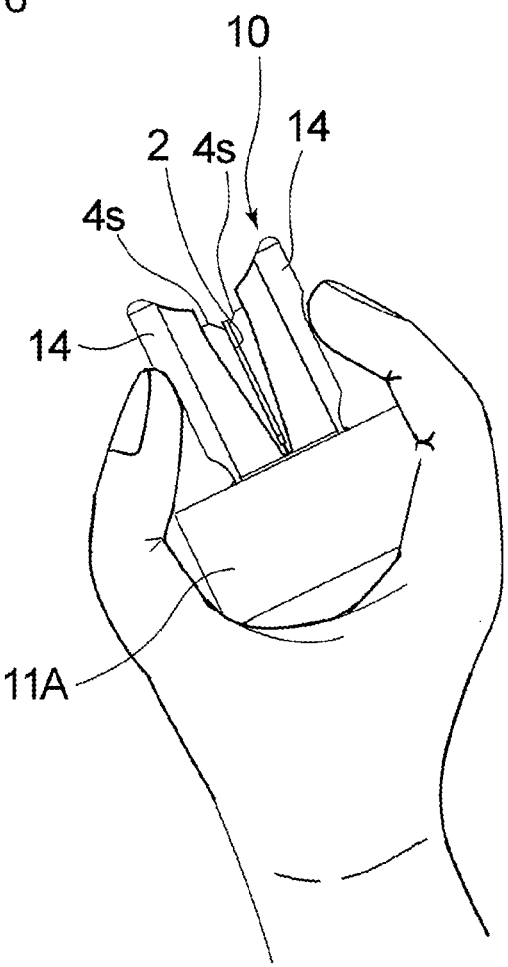
FIG. 6 is a perspective view schematically showing a state in which a degradation inhibitor in liquid form (hereinafter, referred to as "liquid degradation inhibitor") is transferred from an agent holder to a medium holding a specimen by using the cap complex according to the first embodiment.

As shown in FIG. 6, in the first container 1A according to the present embodiment, pressure that presses the agent holder 4 to the medium 2 inserted in the medium-inserted portion 12 can be increased or decreased by increasing or decreasing a pressing force with the pair of outside support portions 14 sandwiched between fingers. Specifically, it is possible to adjust the aforementioned pressure by forming the whole support portion forming member 15 or the outside support portions 14 of a material selected from a relatively soft synthetic resin such as polyethylene, polyester, polypropylene, polyamide synthetic resin, elastomer, or rubber, a composite material of two or more of these or the like. When the pressing force applied to the pair of outside support portions 14 and 14 by fingers is enhanced, a space between the pair of outside support portions 14 and 14 is reduced, and the pressure of the agent holding portions 4s that is pressed against the medium 2 increases. When the pressing force that is applied to the pair of outside support portions 14 and 14 by fingers is weakened on the other hand, the space between the pair of the outside support portions 14 and 14 is enlarged, and the pressure of the agent holding portions 4s that is pressed against the medium 2 is reduced.

From a viewpoint of making the pair of outside support portions 14 and 14 and the agent holding portions 4s held by them movable by the pressing force by the fingers, the pair of outside support portions 14 and 14 preferably have flexible portions 19 at base end sides thereof. The flexible portions 19 are portions to be base points of folding or curving of the outside support portions 14, and are preferably elastically deformable. The flexible portion 19 can be formed by forming the support portion forming member 15 partially thin or the like. Further, the flexible portion 19 can also be formed by providing a hinge structure in a part of the support portion forming member 15. It is also possible to make the flexible portion 19 elastically deformable by placing a rubber-like elastic member, spring, leaf spring or the like at the flexible portion 19. FIG. 6 shows a state in which the pair of outside support portions 14 and 14 are sandwiched between a thumb and a forefinger.

Explaining the outside support portion 14 in the present embodiment in more detail, the pair of outside support portions 14 and 14 each has an inner surface 14a that is a surface on a medium-inserted portion 12 side, an outer surface 14b located on an opposite side to the medium-inserted portion 12 side, and a tip end surface 14c located on an opposite side to the cap section 11A side in a height direction Z of the cap section complex 10.

As shown in FIG. 5 (c), on an inner surface 14a side of each of the pair of outside support portions 14 and 14, a holding depression 14d for the agent holding portion 4s is formed. A part of the agent holding portion 4s is accommodated in the holding depression 14d, and thereby the agent holding portion 4s is stably held in a predetermined position of the outside support portion 14. The agent holding portion 4s accommodated in the holding depression 14d may be fixed into the holding depression 14d by arbitrary means such as bonding by an adhesive, fusion bond, fitting, engagement of engagement projections, or the like. Cross-sectional shapes orthogonal to the height direction Z of the cap section complex 10, of the holding depression 14d and the agent holding portion 4s each can be an arbitrary shape such as a semicircle, a rectangle, or a triangle. The agent holding portions 4s and 4s shown in FIG. 5 (b) are both rectangular in cross-sectional shapes, and the opposing inner surfaces 4a are substantially flat surfaces parallel with each other, but without being limited to this, the inner surfaces 4a opposing each other of the agent holding portions 4s and 4s may curve along one or both of the height direction Z and the first direction X of the cap section complex 10, for example.

The pair of agent holding portions 4s each protrudes from the holding depression 14d on an opposite side to a side accommodated in the holding depression 14d in the agent holder in a state in which a part of an outer surface side of the agent holding portion 4s is accommodated in the holding depression 14d. In other words, a surface on the opposite side to the side accommodated in the holding depression 14d in the agent holding portion 4s, and the inner surface 14a of the outside support portion 14 that supports the agent holding portion 4s are not flush with each other, but the surface on the opposite side to the side accommodated in the holding depression 14d in the agent holding portion 4s is located on the medium-inserted portion 12 side from the inner surface 14a.

As shown in FIG. 5 (a) to FIG. 5 (c), at a time of a state in which a side to which the support portion forming member 15 protrudes from the cap section 11A is located on an upper side in a vertical direction, and a top surface section 11a side of the cap section 11A is located on a lower side in the vertical direction, the height direction Z of the cap section complex 10 is a direction along the vertical direction. In the present embodiment, the height direction Z is substantially parallel with a direction in which the medium 2 is moved when the medium 2 is accommodated in the medium-inserted portion 12. A second direction Y of the cap section complex 10 is a direction orthogonal to the height direction Z of the cap section complex 10, and is a direction in which the pair of outside support portions 14 and 14 or the inner surfaces of the agent holding portions 4s and 4s face each other when the cap section complex 10 is seen in a plan view from one side in the height direction Z, and the first direction X of the cap section complex 10 is a direction orthogonal to the height direction Z of the cap section complex 10, and is a direction orthogonal to the second direction Y when the cap section complex 10 is seen in a plan view from one side in the height direction Z.

As shown in FIG. 5 (c), the support portion forming member 15 in the present embodiment has liquid leak prevention grooves 17 on inner surface 14a sides of the pair of outside support portions 14 and 14. The liquid leak prevention grooves 17 are formed on both sides with the holding depression 14d therebetween in each of the outside support portions 14. The inner surface 14a of the outside support portion 14 is a flat surface on both sides of the holding depression 14d, and the liquid leak prevention grooves 17 are formed on the flat surface. Further, the liquid leak prevention groove 17 extends along the height direction Z of the cap section complex 10. Further, the liquid leak prevention groove 17 terminates at a position short of reaching upper ends of the inner surfaces facing each other of the pair of outside support portions 14 and 14.

The support portion forming member 15 according to the present embodiment has a liquid resupply path for resupplying a liquid passing through the liquid leak prevention groove 17 to the agent holding portion 4s on a base end side in the height direction Z of the cap section complex 10. Specifically, a lower end side of the liquid leak prevention groove 17 communicates with a liquid resupplying space 18 formed on an inner side of the tubular connection portion 11b via a through-hole 17a formed in the base portion 16 of the support portion forming member 15. In the liquid resupplying space 18, an undivided portion 4r of the pair of agent holding portions 4s and 4s is located, and during an operation of transferring the liquid degradation inhibitor 3 to the medium 2 from the agent holder 4, the liquid that is the liquid degradation inhibitor 3 discharged from the agent holding portion 4s and enters the liquid leak prevention groove 17 without remaining in a state of adhering to the medium 2 flows through the liquid leak prevention groove 17, the through-hole 17a and the undivided portion 4r as the liquid resupply path, and is resupplied to the agent holder 4 as shown by arrow "a" in FIG. 5 (c).

The cap section complex 10 according to the present embodiment includes inclined guide surfaces 141 that guide the medium 2 to be inserted into the medium-inserted portion 12 in a direction of an insertion inlet 12a of the medium-inserted portion 12, in a vicinity of upper ends of the pair of outside support portions 14 and 14. The support portion forming member 15 has a pair of inclined guide surfaces 141 on each of both sides with a center portion in the first direction X therebetween, and the pair of inclined guide surfaces 141 each has an inverted taper shape in which a mutual separation distance becomes shorter as a position in the height direction of the support portion forming member 15 becomes lower. The center portions in the first direction X of the pair of outside support portions 14 and 14 have depressed curved surface portions 142 in a shape along a projected curved surface portion of a middle plug 54 that is described later. The inclined guide surface 141 is preferably located on an upper end side of the support portion forming member 15 from the insertion inlet 12a.

The specimen-preserving implement 1 of the present embodiment has the storage 31 of the liquid degradation inhibitor 3 inside of the container body 5A of the first container 1A. Further, a partition portion 50 that divides an internal space of the first container 1A into the storage 31 of the liquid degradation inhibitor 3, and a containing section 53 of the agent holder 4 and the outside support portion 14 is included, and a through-hole 54d penetrating the partition portion 50 is formed in the partition portion 50. The through-hole 54d functions as an agent supply hole for supplying the degradation inhibitor 3 in the storage 31 to the agent holder 4 by the user of the specimen-preserving implement 1 performing a predetermined operation. As the predetermined operation in the present embodiment, there are cited an operation of bringing the first container 1A from a storage state in which the cap section 11A is placed on the upper side in the vertical direction and a bottom portion of the container body 5A is placed on the lower side in the vertical direction to an inverted state in which the cap section 11A and the container body 5A are inverted and leaving the first container 1A for a predetermined time, and an operation of shaking the first container 1A in the inverted state up and down.

It is preferable that the first container 1A has the storage 31 of the degradation inhibitor 3 and the agent holder 4 in a separated state inside, and the storage 31 can be maintained in a state in which the degradation inhibitor 3 and the agent holder 4 are separated until the predetermined operation is performed as above, from a viewpoint of being able to store the degradation inhibitor 3 in a stable state, such as being able to reduce a risk of volatilization and precipitation of the component of the degradation inhibitor 3, for example.

As a configuration that enables the degradation inhibitor 3 and the agent holder 4 to be maintained in a separated state, the method of providing the partition portion 50 between the degradation inhibitor 3 and the agent holder 4 as in the present embodiment is preferable, but only providing the agent holder 4 in the cap section 11A in a self-supporting container and providing the storage of the liquid degradation inhibitor in a site separated in the vertical direction from the agent holder 4 may be adopted.

The partition portion 50 in the present embodiment is formed by placing the middle plug 54 in the container body 5A. The middle plug 54 has an cylindrical portion 54*a* having an outer circumferential surface shape corresponding to an inner circumferential surface shape of the container body 5A, an annular overhang portion 54*b* that abuts on a step portion 55 formed on an inner circumferential surface of the container body 5A to define a mounting position of the middle plug 54, and a dome-shaped tapered portion 54*c* in which an inside diameter and an outside diameter gradually decrease toward one end opening side of the container body 5A, and the aforementioned through-hole 54*d* is formed in a top portion of the tapered portion 54*c*.

From a viewpoint of transference of the degradation inhibitor 3 to the agent holding portion 4*s* from the storage 31, in the partition portion 50, a surface side facing the agent holder 4, of the tapered portion 54*c* is preferably formed into a shape along the pair of inclined guide surfaces 141 in the aforementioned outside support portion 14. Further, from the same viewpoint, in the partition portion 50 and the middle plug 54, a position of the through-hole 54*d* is preferably formed in a position facing the medium-inserted portion 12 in the agent holder 4. Further, from a viewpoint of preventing the degradation inhibitor 3 in the storage 31 from being transferred to the agent holder 4 until the user intentionally performs a predetermined operation, an opening area of the through-hole 54*d* as the agent supply hole formed in the middle plug 54 is preferably smaller than an opening area on a storage 31 side, in the middle plug 54, the opening area of the through-hole 54*d* (agent supply hole) is preferably 10% or less of the opening area on the storage 31 side, and more preferably 5% or less.

As shown in FIG. 1 and FIG. 2 (*b*), the second container 1B in the first embodiment has a cap section 11B and a container body 5B to which the cap section 11B is fitted.

As shown in FIG. 4, to the container body 5B of the second container 1B, the cap section 11A detached from the container body 5A of the first container 1A is finable. As in the second container 1B in the present embodiment, a cap section 11B different from the cap section 11A of the first container 1A is preferably fitted to the container body 5B of the second container 1B before the cap section 11A of the first container 1A is fitted to close an opening of the container body 5B. The cap section 11B of the second container 1B in the present embodiment is fitted to one end opening of the container body 5B detachably or detachably and attachably.

The container body 5B in the second container 1B has a similar size and configuration to the container body 5A of the first container 1A, except that a containing section 6 of desiccant and a contact-suppressing member 7 are placed, and that the container body has a different identification representation 9, although the agent holder 4, the support portion forming member 15, the middle plug 54 and the storage 31 of the degradation inhibitor in the first container 1A are not formed inside. As shown in FIG. 3, it is possible to form a storage container 1C in which the cap section 11A of the first container 1A and the container body 5B of the second container 1B are combined by detaching the cap section 11A from the container body 5A in the first container 1A and inserting the medium 2 holding the specimen into the medium-inserted portion 12 attached to the cap section 11A, thereafter, fitting the cap section 11A to the one end opening of the container body 5B of the second container 1B.

In the first container 1A, screw lines 21 and 58 are provided in an inner circumferential surface of the cap section 11A and an outer circumferential surface of the one end opening of the container body 5A, and the cap section 11A is screwed onto the container body 5A. A seal member such as packing not illustrated is placed on each of collision portions of the cap section 11A and the container body 5A, and each of collision portions of the cap section 11B and the container body 5B so that insides of the first container 1A, the second container 1B and the storage container 1C can be airtightly sealed by fitting of the cap section 11A. A method for mounting the cap section 11A or 11B to the container body 5A or the container body 5B is not limited to screwing, but any configuration such as engagement or fitting can be adopted.

The containing section 6 of the desiccant in the second container 1B is formed in a vicinity of a bottom portion of the container body 5B, and as shown in FIG. 4, when the cap section 11A of the first container 1A to which the medium 2 holding the specimen and the agent holder 4 are attached is fitted to the container body 5B, the contact-suppressing member 7 is located between the agent holder 4 and the containing section 6 of the desiccant so that a desiccant 61 in the containing section 6 does not directly contact the agent holder 4.

The contact-suppressing member 7 can absorb humidity released from the agent holder 4 or the degradation inhibitor transferring to the medium 2 from the agent holder 4 while it can separate the desiccant 61 from the agent holder 4 so that they do not directly contact each other, and a member in any form formed of any material can be used as long as the member can achieve such a purpose. The contact-suppressing member 7 is of a material that does not inhibit air permeability between the desiccant of the containing section 6 of the desiccant and the agent holder 4. As the contact-suppressing member 7, a porous member fixed to a predetermined height position of an internal space of the container body 5B, a middle plug, a cotton-like body formed of a synthetic resin, a sheet-like member having air permeability and the like are cited.

As the desiccant 61, a desiccant that can absorb moisture and humidity released from the degradation inhibitor can be used without particular limitation. As the desiccant 61, it is possible to use, for example, a physical desiccant such as silica gel, aluminum oxide, molecular sieve, or zeolite, or a chemical desiccant such as quick lime, or calcium chloride. As the desiccant 61, it is also possible to use one kind alone, or two or more kinds in combination. The chemical desiccant is accompanied by change in substance when drying, while the physical desiccant adsorbs water molecules on a porous surface without change in substance, so that as the desiccant 61, use of the physical desiccant such as a molecular sieve is preferable, from a viewpoint of reliably suppressing an influence on the specimen or medium.

By using the desiccant 61, it is possible to inhibit degradation of the component to be tested due to hydrolysis with reaction promoted under presence of moisture more effectively.

As the degradation inhibitor 3, a solution of the degradation inhibitor 3 or the like having a function of inhibiting degradation of a component to be tested that may be contained in the medium can be used without limitation. For example, when the specimen contains enzymes that degrade the component to be tested, various liquid agents that can inhibit or inactivate activity of the enzymes can be used. When the specimen is sebum, and the component to be tested contained in the specimen is a nucleic acid, the sebum may contain nucleolytic enzymes derived from the subject or other germs. It is possible to inhibit degradation of nucleic acids contained in the specimen by inactivating such nucleolytic enzymes. As the degradation inhibitor 3 in the case of the component to be tested being a nucleic acid, an aqueous solution containing guanidine hydrochloride that is a chaotropic denaturant, guanidine thiocyanate, urea or thiourea, or the like can be used. Since it is not preferable that an aqueous solution or the like containing guanidine hydrochloride contacts a body, it is more useful to use the specimen-preserving implement 1 of the present invention when using such a degradation inhibitor, from a viewpoint of being able to inhibit the degradation inhibitor from adhering to a body. An amount of a liquid of the degradation inhibitor 3 that is accommodated in the first container 1A can be properly determined according to a size of the medium 2 or the like. For example, FIG. 2 (a) shows a state in which about 1 to 2 mL of the liquid degradation inhibitor 3 is accommodated.

Concerning a method of using the specimen-preserving implement 1 of the first embodiment, a preferable example is shown and described.

First, the medium 2A is caused to hold a specimen such as sebum by an appropriate method such as wiping a surface of the subject with the medium 2A capable of holding the specimen. In a case of the sheet-like medium 2A, the medium 2A is folded up a plurality of times into a compact form.

After the agent holder 4 is impregnated with the degradation inhibitor 3 accommodated in the storage 31 in the first container 1A by a predetermined operation of inverting the first container 1A and shaking the first container 1A up and down a plurality of times, the cap section 11A is detached from the container body 5A in the first container 1A, and the medium 2 holding the specimen is inserted into the medium-inserted portion 12 provided in the agent holder 4 attached to the cap section 11A.

Since the agent holder 4 is impregnated with the liquid degradation inhibitor 3, the liquid degradation inhibitor 3 efficiently transfers to the medium 2 by inserting the medium 2 into the medium-inserted portion 12 formed in the agent holder 4.

By sandwiching the outside support portions 14 and 14 between fingers in the state in which the medium 2 is inserted into the medium-inserted portion 12, and pressing the outside support portions 14 and 14, it is possible to transfer the liquid degradation inhibitor 3 with which the agent holder 4 is impregnated to the medium 2 and the specimen held by the medium 2 more effectively. By sandwiching the outside support portions 14 and 14 between the fingers and repeatedly increasing or decreasing the pressing force, it is possible to transfer the liquid degradation inhibitor 3 with which the agent holder 4 is impregnated to the medium 2 more reliably and efficiently.

Next, the cap section 11A of the first container 1A that holds the agent holder 4 and the medium 2 in a state of contacting each other is fitted to the container body 5B of the second container 1B in which the desiccant is accommodated inside with the cap section 11B detached. By fitting the cap section 11A of the first container 1A to the one end opening of the container body 5B of the second container 1B, the cap section 11A of the first container 1A and the container body 5B of the second container 1B are combined to form the storage container 1C with an interior airtightly sealed.

According to the specimen-preserving implement 1 of the first embodiment, it is possible to transfer the liquid degradation inhibitor 3 to the medium 2 from the agent holder 4 by inserting the medium 2 holding the specimen into the medium-inserted portion 12 as described above, so that it is possible to inhibit degradation of the component to be tested in the specimen contained in the medium 2. Further, using the liquid degradation inhibitor 3 is preferable from a viewpoint of being able to efficiently impregnate the agent holder 4 and a viewpoint of being able to efficiently transfer the degradation inhibitor 3 with which the agent holder 4 is impregnated to the medium 2.

In addition, the medium 2 contacts the agent holder 4 impregnated with the liquid degradation inhibitor 3 and thereby the degradation inhibitor 3 transfers to the medium 2, instead of directly bringing the liquid degradation inhibitor 3 into contact with the medium 2 and the specimen, so that it is possible to prevent the liquid degradation inhibitor 3 from spilling or scattering around during an operation of bringing the degradation inhibitor 3 into contact with the medium 2.

Further, according to the specimen-preserving implement 1 of the first embodiment, it is possible to store the medium 2 in an airtight state in the storage container 1C generated by fitting the cap section 11A after the medium 2 is inserted into the medium-inserted portion 12 to the container body 5B of the second container 1B, and it is possible to absorb humidity released from the degradation inhibitor 3 by the desiccant 61 without directly bringing the desiccant 61 into contact with the agent holder 4 under the state in which the medium 2 is accommodated in the medium-inserted portion 12. Thereby, it is possible to reduce the amount of moisture in the liquid degradation inhibitor remaining in the agent holder 4 without directly bringing the desiccant 61 into contact with the liquid degradation inhibitor remaining in the agent holder 4, it is possible to inhibit hydrolysis of the component to be tested that occurs by enzymes or naturally, for example, and it is possible to inhibit degradation of the component to be tested more reliably. Further, even if the component to be tested degrades without hydrolysis, it is possible to reduce a possibility that the degradation inhibitor 3 leaks during storage and transportation, owing to reduction in the amount of moisture in the liquid degradation inhibitor remaining in the agent holder 4.

In this way, according to the specimen-preserving implement 1 of the first embodiment, it is possible to prevent contact of the liquid degradation inhibitor 3 with a body by impregnating the agent holder 4 with the liquid degradation inhibitor 3 and bringing the agent holder 4 into contact with the medium 2, and it is possible to more effectively inhibit leak of the liquid degradation inhibitor and degradation of the component to be tested in the specimen by reducing moisture in the liquid degradation inhibitor after the medium is accommodated. Further, according to the specimen-preserving implement 1 of the first embodiment, cooling equipment is not necessary, and excellent workability is provided for accommodation and transportation of the specimen.

Further, the second container 1B has the contact-suppressing member 7 that is placed between the containing section 6 of the desiccant and the agent holder 4, and inhibits contact of the desiccant 61 and the agent holder 4 to prevent the desiccant 61 from directly contacting the agent holder 4, and this has an advantage of being able to inhibit occurrence of various troubles that can occur depending on the combination of the liquid degradation inhibitor 3 and the desiccant 61 such as heat generation occurring due to direct contact of an aqueous solution of guanidine hydrochloride and a molecular sieve, or the like.

Next, specimen-preserving implements of a second to a seventh embodiments of the present invention are described. For the second to a fifth embodiments, different points from the first embodiment are described, and similar points are assigned with the same reference signs and explanations thereof are omitted.

Figure 7:
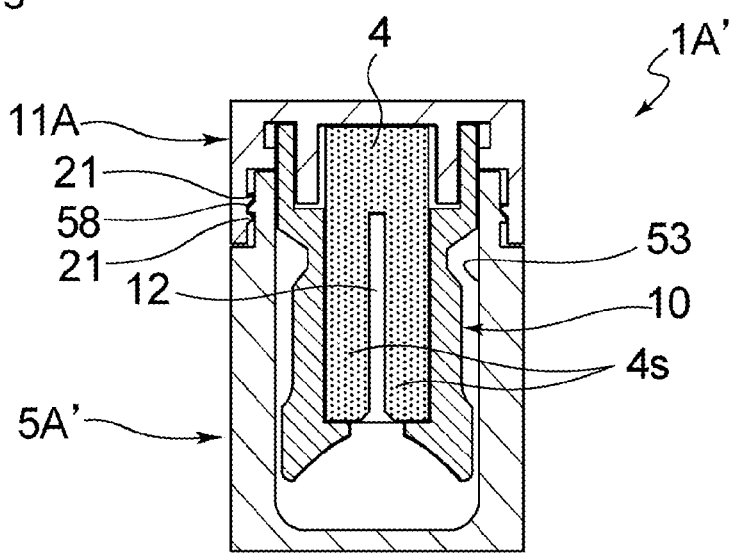
FIG. 7 is a sectional view showing a specimen-preserving implement according to a second embodiment of the present invention, and is a view corresponding to FIG. 2 (a).

A specimen-preserving implement of the second embodiment differs from the first embodiment in a point of including a first container 1A' shown in FIG. 7 instead of the first container 1A shown in FIG. 2 (a).

The first container 1A' shown in FIG. 7 does not have a middle plug inside, and a liquid degradation inhibitor is held in a state of being impregnated in the agent holder 4. In the specimen-preserving implement of the second embodiment, it is also possible to provide a storage container in which a cap section 11A of the first container 1A' and a container body 5B of a second container 1B are combined by detaching the cap section 11A from a container body 5A' of the first container 1A', inserting a medium 2 holding a specimen into a medium-inserted portion 12 attached to the cap section 11A, and thereafter, fitting the cap section 11A to one end opening of the container body 5B of the second container 1B similar to those in the first embodiment.

According to the second embodiment, a similar effect as the effect of the first embodiment is provided, except for an effect by separation of the degradation inhibitor and the agent holder before use.

Further, the first container 1A' in the second embodiment differs in height from the second container 1B, so that distinguishing between the first container 1A' and the second container 1B is easier, and confusion can be more reliably prevented. Note that a height of the first container 1A' and a height of the second container 1B may be the same.

Figure 8:
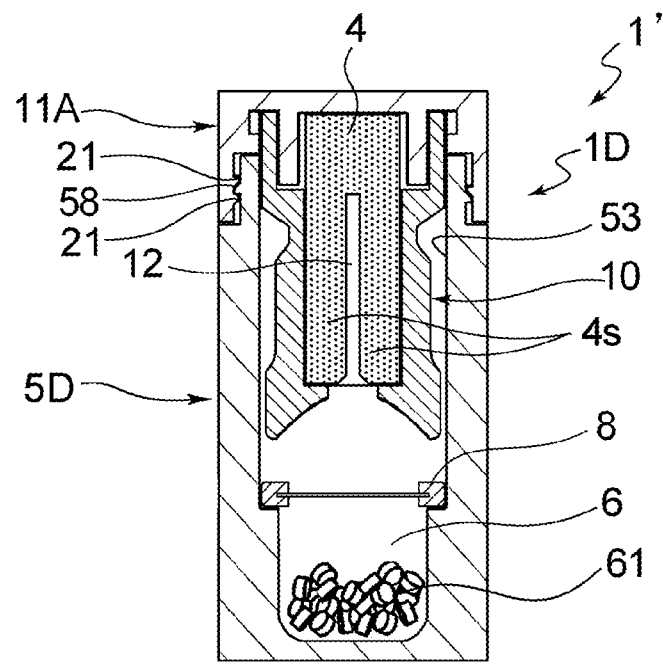
FIG. 8 is a sectional view showing a specimen-preserving implement according to a third embodiment of the present invention, and is a view corresponding to FIG. 2 (a).

As shown in FIG. 8, a specimen-preserving implement 1' of a third embodiment has a medium-inserted portion 12 as a medium-containing section, a liquid degradation inhibitor 3 that inhibits degradation of a sample to be tested contained in a medium, an agent holder 4 that can be impregnated with the degradation inhibitor 3, and a containing section 6 of a desiccant, in a single container 1D. The container 1D has a cap section 11A holding the agent holder 4 and a container body 5D to which the cap section 11A is fitted detachably and attachably. A medium-inserted portion 12 is provided in the agent holder 4 held by the cap section 11A. In the specimen-preserving implement 1', the agent holder 4 is impregnated with a suitable amount of the degradation inhibitor 3 in advance before use of the specimen-preserving implement. Further, inside of the container body 5D, a partition member 8 that inhibits contact of a desiccant 61 in the containing section 6 and the agent holder 4 is placed. The partition member 8 provides an airtight separation between the agent holder 4 and the containing section 6 of the desiccant, so that moisture of the degradation inhibitor impregnated to the agent holder 4 is not absorbed by the desiccant 61 before use. Thereby, the degradation inhibitor is maintained in a liquid state, and transfer of the degradation inhibitor to the medium 2 from the agent holder 4 becomes good. The partition member 8 is, for example, an annular member including a thin membrane of a synthetic resin in a center portion.

At a time of use of the specimen-preserving implement 1' of the third embodiment, the cap section 11A is detached from the container body 5D, the medium 2 after a specimen is held in a sheet-like medium 2A' is folded up into an appropriate size and inserted into the medium-inserted portion 12 of the agent holder 4 impregnated with the liquid degradation inhibitor 3 in advance, outside support portions 14 and 14 are pressed with fingers as desired, and transfer of the degradation inhibitor 3 to the medium 2 from the agent holder 4 is promoted. Further, in the partition member 8 in the container body 5D from which the cap section 11A is detached, a through-hole is formed by an appropriate puncture tool such as a toothpick, or an exclusive puncture tool supplied as a set with the specimen-preserving implement 1'. The partition member 8 in which the through-hole is formed functions as a contact-suppressing member.

Subsequently, the cap section 11A in which the medium 2 is held in the medium-inserted portion 12 is fitted to the container body 5D.

In this way, in the specimen-preserving implement 1' of the third embodiment, the degradation inhibitor 3 is also caused to transfer to the medium 2 by placing the medium 2 in the medium-inserted portion (medium-containing section) 12 under the state in which the agent holder 4 is impregnated with the liquid degradation inhibitor 3, and the desiccant 61 is caused to be able to absorb humidity released from the degradation inhibitor 3 without directly contacting the agent holder 4 under the state in which the medium 2 is accommodated in the medium-inserted portion (medium-containing section) 12. Therefore, according to the specimen-preserving implement 1' of the third embodiment, a similar effect to the effect of the specimen-preserving implement of the first or the second embodiment is exhibited. Further, the two containers that are the first container and the second container are not required, which is advantageous in transportation, storage, handling and the like.

Figure 9:
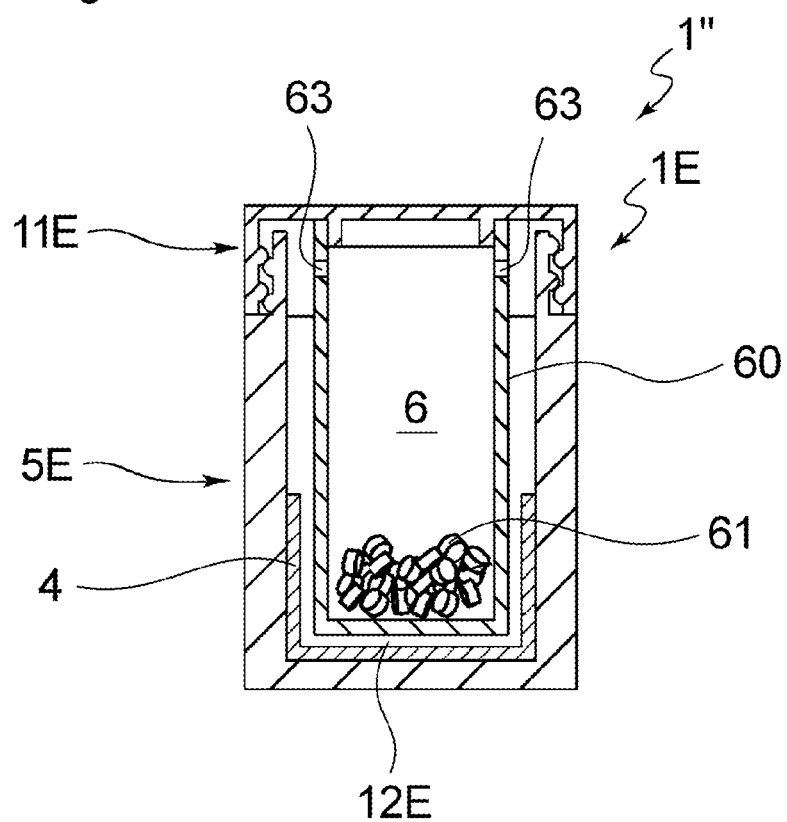
FIG. 9 is a sectional view showing a specimen-preserving implement according to a fourth embodiment of the present invention, and is a view corresponding to FIG. 2 (a).

As shown in FIG. 9, a specimen-preserving implement 1" of a fourth embodiment includes a container 1E having a cap section 11E and a container body 5E to which the cap section is fitted. The cap section 11E is detachably and attachably fitted to one end opening of the container body 5E in a bottomed cylindrical shape.

The cap section 11E is provided with a desiccant-containing body 60 in a bottomed cylindrical shape having a containing section 6 of a desiccant, inside. The desiccant-containing body 60 functions as a contact-suppressing member that inhibits direct contact of an agent holder 4 impregnated with a liquid degradation inhibitor and a desiccant 61. In the container body 5E, the agent holder 4 in a state of being impregnated with the liquid degradation inhibitor is placed. The agent holder 4 has a part placed along a top surface of a bottom portion of the container body 5E and an inner circumferential surface in a vicinity of the bottom portion. As shown in FIG. 9, a space between the desiccant-containing body 60 and the agent holder 4 in a state in which the cap section 11E is fitted to the container body 5E is a medium-containing section 12E in which a medium 2 holding a specimen is accommodated.

The desiccant-containing body 60 is formed of an agent-impermeable material impermeable to the degradation inhibitor, and ventilation holes 63 that communicate with an inside and an outside of the containing section 6 of the desiccant are formed in sites that do not contact the medium 2.

The ventilation hole 63 is closed with a seal or the like (not illustrated) in a state before the medium is put in, and after the cap section 11E is detached, the seal or the like is removed before the medium 2 is accommodated to bring the ventilation hole 63 into a ventilatable state. The ventilation hole 63 is formed in a site on a cap section 11E side in the desiccant-containing body 60. A plurality of ventilation holes 63 are formed to be spaced apart in a circumferential direction around the desiccant-containing body 60. The number of ventilation holes 63 may be only one.

Figure 10:
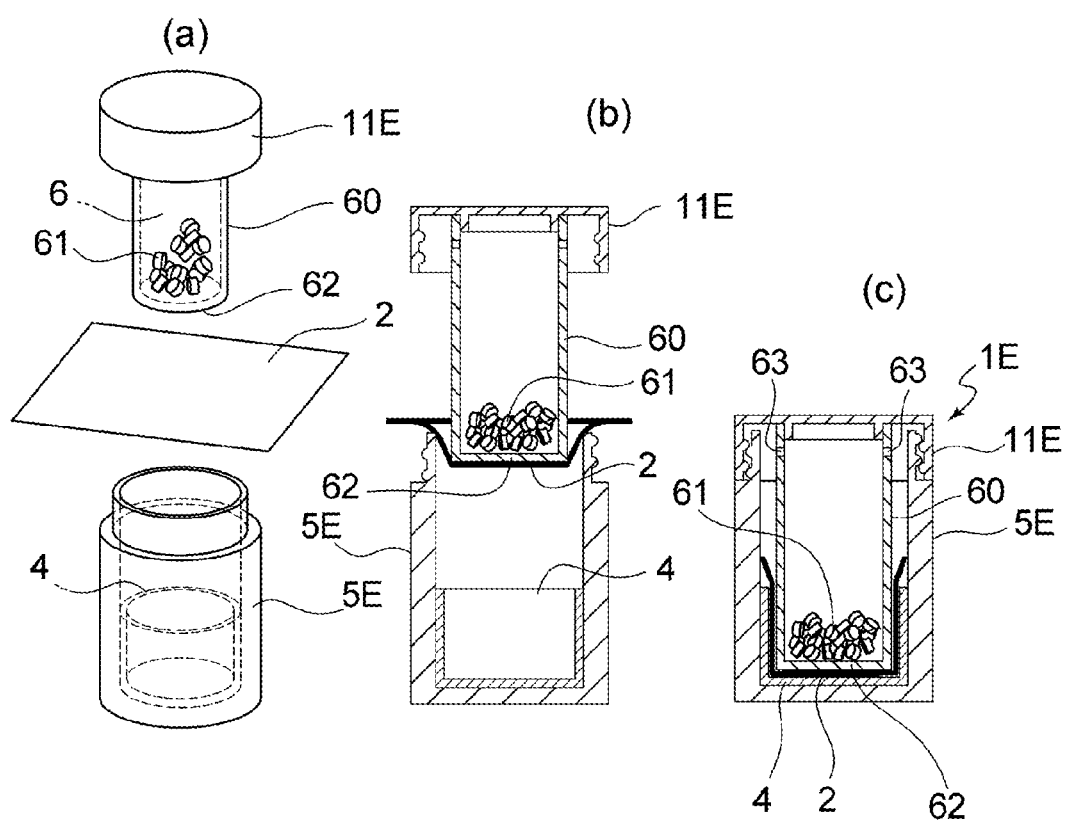
FIG. 10 (a) to FIG. 10 (c) are views schematically showing a state in which a liquid degradation inhibitor is transferred from an agent holder to a medium holding a specimen by using the specimen-preserving implement according to the fourth embodiment of the present invention, FIG. 10 (a) is a perspective view, and FIG. 10 (b) and FIG. 10 (c) are sectional views.

At a time of using the specimen-preserving implement 1" of the fourth embodiment, the cap section 11E is detached from the container body 5E, the medium 2 which is folded up into an appropriate size after causing a sheet-like medium 2' to hold the specimen is located under a bottom portion 62 of the desiccant-containing body 60 attached to the cap section 11E as shown in FIG. 10 (a), the medium 2 is pushed into the container body 5E with the desiccant-containing body 60 as shown in FIG. 10 (b), the medium 2 is pressed against and closely contacted to the agent holder 4 by the desiccant-containing body 60, and the cap section 11E is fitted to the container body 5E to hermetically close a space in the container 1E as shown in FIG. 10 (c).

According to the specimen-preserving implement 1" of the fourth embodiment, the medium 2 can be placed in the medium-containing section 12E under the state in which the agent holder 4 is impregnated with the liquid degradation inhibitor 3, and thereby the degradation inhibitor 3 transfers to the medium 2. Further, as shown in FIG. 10 (c), in the container 1E in which the inside is hermetically closed, the desiccant 61 absorbs humidity released from the degradation inhibitor 3 via the ventilation holes 63 without directly contacting the agent holder 4. In this way, according to the specimen-preserving implement 1" of the fourth embodiment, same effects to the effects of the specimen-preserving implements of the first to the third embodiments are exhibited.

Instead of locating the sheet-like medium 2 holding the specimen under the bottom portion 62 of the desiccant-containing body 60, the sheet-like medium 2 is brought into a state wound around a periphery of a lower portion of the desiccant-containing body 60 and that medium 2 may be pushed into a space surrounded by the agent holder 4 in the container body 5E and brought into close contact with the agent holder 4.

Figure 11:
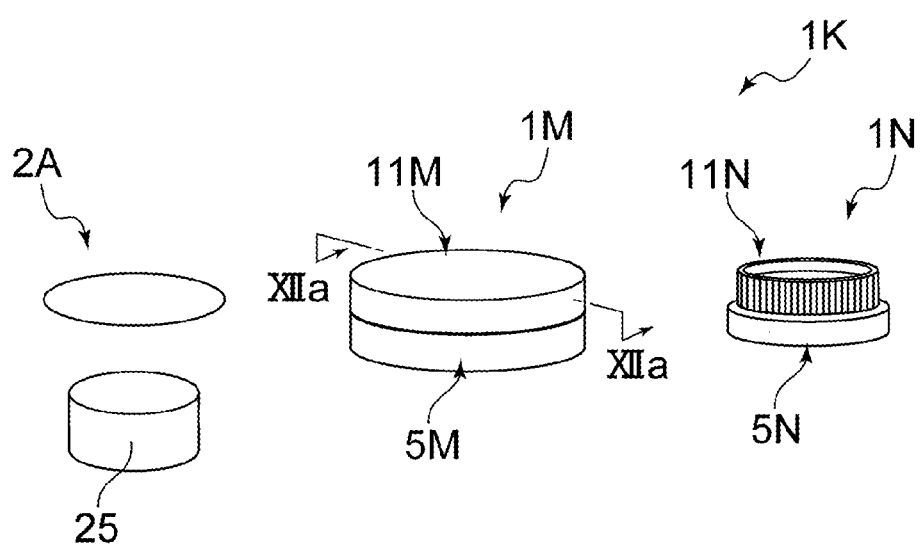
FIG. 11 is a perspective view showing a specimen-preserving implement of a fifth embodiment of the present invention and is a view corresponding to FIG. 1.

FIG. 11 is a view showing a specimen-preserving implement 1K of a fifth embodiment of the present invention. The specimen-preserving implement 1K of the fifth embodiment includes a first container 1M having a cap section 11M and a container body 5M to which the cap section 11M is fitted, and an inner container 5N that is accommodated in the first container 1M. The inner container 5N is combined with a cap section 11N to configure a second container 1N.

The specimen-preserving implement 1K of the fifth embodiment is preferably provided to a user as a set of the first container 1M and the second container 1N.

The specimen-preserving implement 1K of the fifth embodiment has an agent holder 4 capable of being impregnated with a liquid degradation inhibitor in the first container 1M, and a part of the inner container 5N is a desiccant-containing body 60 having a containing section 6 of a desiccant.

Figure 14:
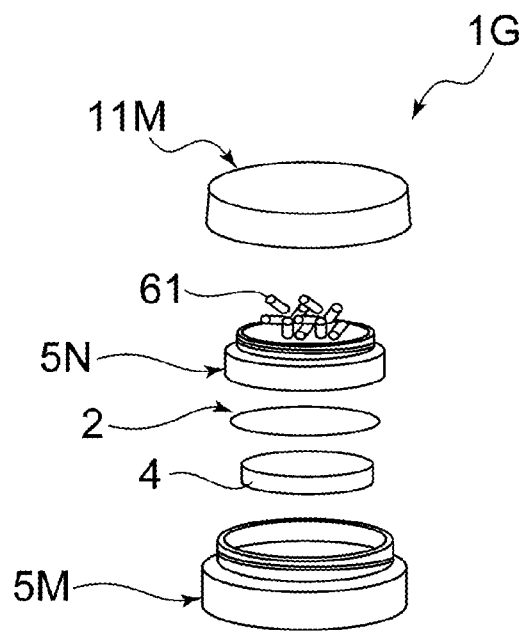
FIG. 14 (*a*) and FIG. 14 (*b*) are views schematically showing a state where a liquid degradation inhibitor is transferred from an agent holder to a medium holding a specimen by using the specimen-preserving implement according to the fifth embodiment of the present invention, FIG. 14 (*a*) is an exploded perspective view, and FIG. 14 (*b*) is a sectional view.
Figure 14:
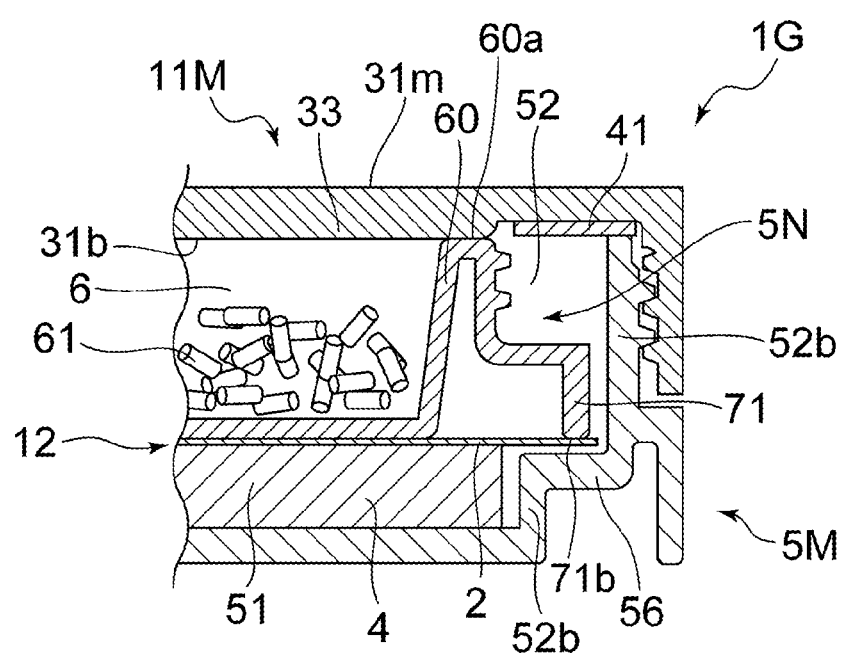

As shown in FIG. 14 (a) and FIG. 14 (b), the specimen-preserving implement 1K of the fifth embodiment can be formed as a storage container 1G in which the inner container 5N is accommodated in the first container 1M, by detaching the cap section 11M from the container body 5M in the first container 1M, placing a medium 2 holding a specimen on the agent holder 4 that is accommodated in a holder containing section 51 of the container body 5M, placing the inner container 5N accommodating a desiccant 61 in a container containing section 52 of the container body 5M, and thereafter fitting the cap section 11M of the first container 1M to one end opening of the container body 5M.

Figure 12:
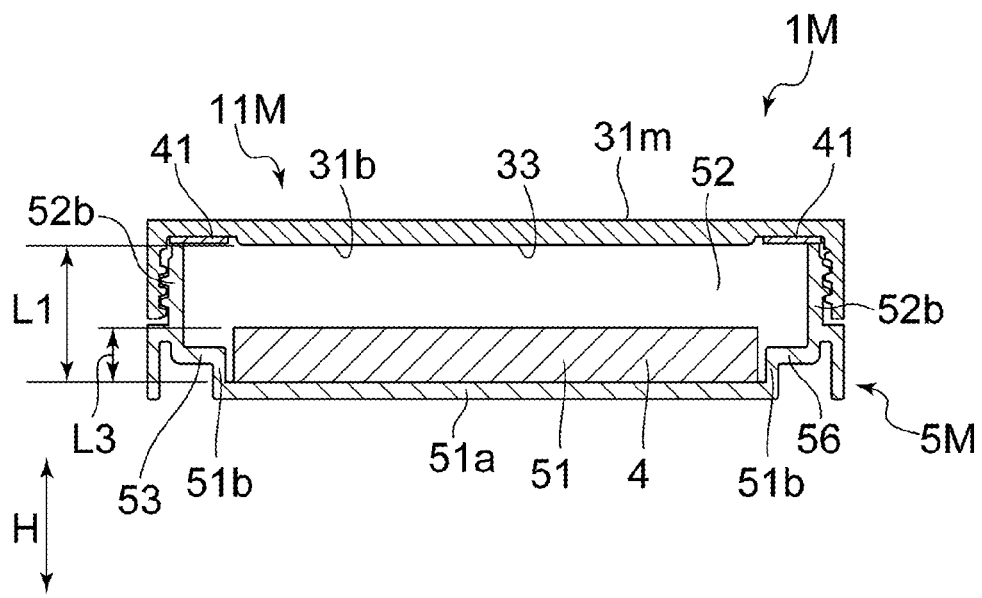
FIG. 12 (*a*) and FIG. 12 (*b*) are views schematically showing a first container shown in FIG. 11, FIG. 12 (*a*) is a sectional view taken along line XIIa-XIIa of the first container shown in FIG. 11, and FIG. 12 (*b*) is a plan view of a cap section of the first container shown in FIG. 11 seen from a back surface side.
Figure 12:
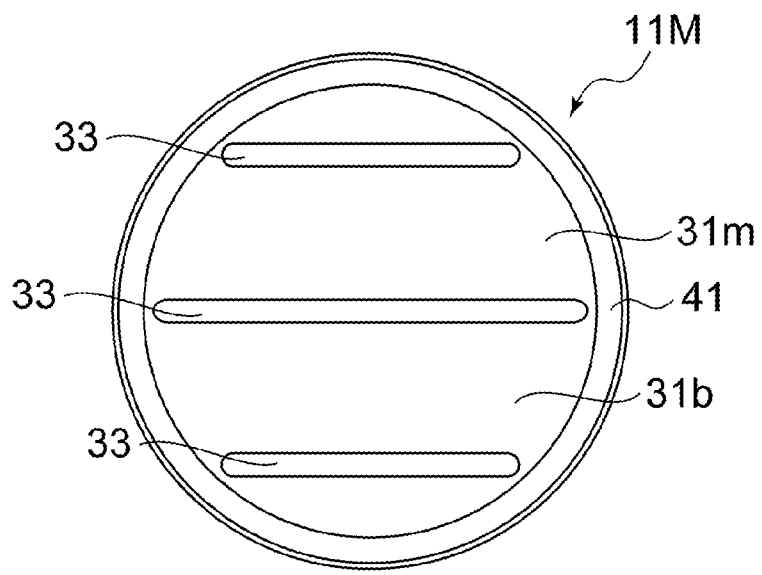

As shown in FIG. 11 and FIG. 12 (a), the first container 1M has the cap section 11M and the container body 5M to which the cap section 11M is fitted. The cap section 11M is fitted to the one end opening of the container body 5M in a bottomed cylindrical shape detachably and attachably.

As shown in FIG. 12 (a) and FIG. 12 (b), the cap section 11M has a seal member 41 on a back surface 31b side of a top surface section 31m. The seal member 41 has a shape in a plan view along a perimeter shape of an opening of the inner container 5N, and has a substantially circular annular shape. The seal member 41 is placed at a perimeter portion of the top surface section 31m of the cap section 11M. As the seal member 41, packing or the like formed of a material such as a rubber, silicone, elastomer, polyethylene, foamed polyethylene, polypropylene, or foamed polypropylene is cited.

Further, as shown in FIG. 12 (a) and FIG. 12 (b), the cap section 11M has a convex stripe portion 33 that protrudes from the back surface 31b of the top surface section 31m. The convex stripe portion 33 extends along one direction. In the fifth embodiment, the convex stripe portion 33 is placed in a region surrounded by the seal member 41. Further, an end portion 33a in a longitudinal direction of the convex stripe portion 33 does not reach the seal member 41. In other words, a gap is formed between the end portion 33a in the longitudinal direction of the convex stripe portion 33 and the seal member 41.

The cap section 11M may have the only one convex stripe portion 33, or may have a plurality of convex stripe portions 33. When the cap section 11M has a plurality of convex stripe portions 33, directions in which the plurality of convex stripe portions 33 extend may cross one another, or may be substantially parallel with one another as shown in FIG. 12 (b).

As shown in FIG. 12 (a), the container body 5M has the holder containing section 51 capable of accommodating the agent holder 4, and the container containing section 52 capable of accommodating the inner container 5N. The container containing section 52 is located on an opening side of the container body 5M from the holder containing section 51. In the fifth embodiment, the holder containing section 51 is a space surrounded by a bottom portion 51a of the container body 5M and a first circumferential wall portion 51b provided to be raised from a perimeter portion of the bottom portion 51a. The container containing section 52 is a space surrounded by a second circumferential wall portion 52b located on an opening side of the container body 5M from the first circumferential wall portion 51b. The second circumferential wall portion 52b has a larger diameter than the first circumferential wall portion 51b. A lower end portion of the second circumferential wall portion 52b and an upper end section of the first circumferential wall portion 51b are connected by a connection portion 56.

Figure 13:
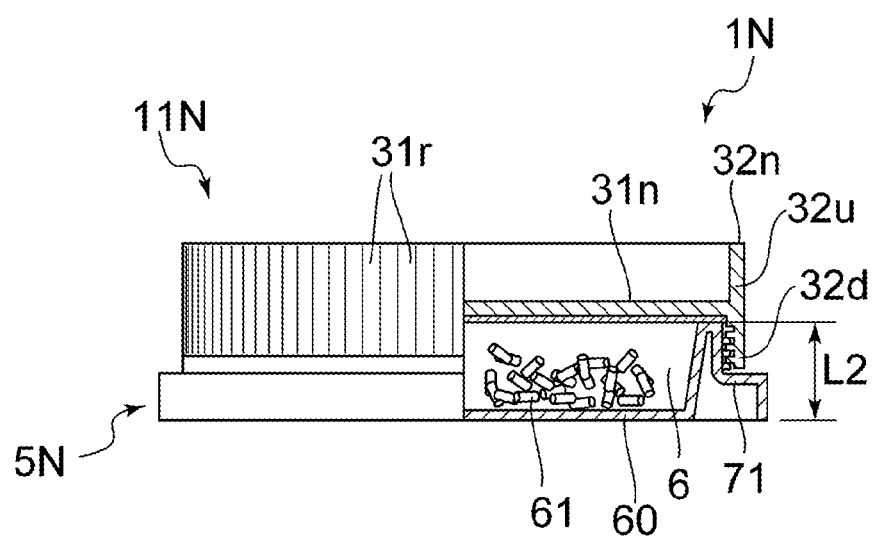
FIG. 13 is a side view showing a second container shown in FIG. 11 with a part cut away.

As shown in FIG. 13, the second container 1N has the cap section 11N and the inner container 5N to which the cap section 11N is fitted. The cap section 11N is fitted to the opening of the inner container 5N in a bottomed cylindrical shape detachably and attachably.

The inner container 5N is configured to be accommodated in the container containing section 52 of the container body 5M of the first container 1M (see FIG. 14 (a) and FIG. 14 (b)).

As shown in FIG. 13, the inner container 5N has a desiccant-containing body 60 having a containing section 6 of a desiccant 61 inside. The desiccant-containing body 60, when placed inside the container body 5M of the first container 1M, functions as a contact-suppressing member that inhibits direct contact of the agent holder 4 impregnated with a liquid degradation inhibitor and the desiccant 61.

The inner container 5N has a container circumferential wall portion 71 in addition to the desiccant-containing body 60. The container circumferential wall portion 71 is located outward in a radial direction of the inner container 5N from the desiccant-containing body 60.

The cap section 11N has a top surface section 31*n* and a circumferential wall portion 32*n* provided to extend from a perimeter portion of the top surface section 31*n*. The circumferential wall portion 32*n* is provided to extend to both sides in a height direction H of the cap section 11N from the perimeter portion of the top surface section 31*n*. In other words, the circumferential wall portion 32*n* includes an upper side circumferential wall portion 32*u* located at an upper side in the height direction H from the top surface section 31*n*, and a lower side circumferential wall portion 32*d* located at a lower side in the height direction H from the top surface section 31*n*. An advantage of the circumferential wall portion 32*n* of the cap section 11N having the upper side circumferential wall portion 32*u* is as follows. Even if a length in the height direction H of the lower side circumferential wall portion 32*d* is so short that the user cannot grasp the lower side circumferential wall portion 32*d*, a length in the height direction H of the circumferential wall portion 32*n* can be made long enough for the user to grasp the circumferential wall portion 32*n*. If the user can grasp the circumferential wall portion 32*n*, the user can grasp the circumferential wall portion 32*n*, and turn the cap section 11N with respect to the inner container 5N, so that it becomes easier to attach and detach the cap section 11N to and from the inner container 5N. From a viewpoint of the user grasping the circumferential wall portion 32*n* more easily, the circumferential wall portion 32 preferably has ribs 31*r* on an outer surface thereof, as shown in FIG. 11 and FIG. 13.

As shown in FIG. 14 (*a*) and FIG. 14 (*b*), in the specimen-preserving implement 1K of the fifth embodiment, the medium-containing section 12 is formed between the desiccant-containing body 60 and the agent holder 4 in the state in which the inner container 5N is accommodated in the container body 5M and the cap section 11M is fitted to the container body 5M. The medium-containing section in the specimen-preserving implement of the present invention also includes a medium-containing section that is formed by combining a plurality of members that configure the specimen-preserving implement 1K, for example, combining the first container 1M and the inner container 5N in the present embodiment without being limited to the medium-containing section that is originally formed like the medium-inserted portion 12 of the first embodiment.

As shown in FIG. 14 (*a*) and FIG. 14 (*b*), in the specimen-preserving implement 1K of the fifth embodiment, the medium 2 is brought into close contact with the agent holder 4 by removing the cap section 11M from the container body 5M in the first container 1M, placing the medium 2 between the desiccant-containing body 60 and the agent holder 4, and thereafter, fitting the cap section 11M to the container body 5M.

A method for using the specimen-preserving implement 1K of the fifth embodiment is described by showing a preferable example.

First, by an appropriate method such as wiping out a surface of a subject with the medium 2A capable of holding a specimen, the medium 2A is caused to hold the specimen such as sebum. When an operation of wiping out the surface of the subject by the medium 2A or the like is performed, an auxiliary tool 25 that can hold the medium 2A detachably and attachably is also preferably used.

By using the auxiliary tool 25, the user can perform an operation of wiping out the surface of the subject by grasping the auxiliary tool 25 without directly grasping the medium 2A, so that substances other than the specimen can be prevented from adhering to the medium 2A.

The auxiliary tool 25 preferably has cushioning properties. Further, the auxiliary tool 25 can preferably bond the medium 2A without using an adhesive. As the auxiliary tool 25, various synthetic resin foams having cushioning properties can be used, and it is possible to preferably use a tool that is formed by pasting a material having a suction cup structure or the like having, on a surface thereof, numerous recesses in which interiors are brought into a decompressed state by pressure contact, on a material having cushioning properties. As the material having cushioning properties, for example, elastic resin form is cited, and foam or the like containing ethylene propylene diene copolymer (EPDM), NBR, PE, PP, PET, SBR, elastomer, silicone rubber or the like as a raw material is specifically cited. Further, the material having cushioning properties is preferably a sponge formed of a synthetic resin or a natural material having an elastic restoring force to compression, nonwoven fabric, woven fabric, a composite material using two or more of these materials that are selected, or the like. As the material having a suction cup structure, acrylic resin or the like is cited.

A shape of the auxiliary tool 25 that can hold the medium 2A is not particularly limited, and, for example, a rectangular parallelepiped, a column, a hemisphere, and the like are cited. The column or the like may be in a flattened shape as shown in FIG. 11. A sectional shape of the rectangular parallelepiped or the column is not particularly limited, and may be a circle (see FIG. 11), an ellipse, a rectangle, a rhombus or the like.

The cap section 11M is detached from the container body 5M in the first container 1M, and the medium 2 holding the specimen is placed on the agent holder 4 impregnated with the degradation inhibitor 3 (see FIGS. 14 (*a*) and (*b*)). When the medium 2 is held by the auxiliary tool 25, the medium 2 is detached from the auxiliary tool 25, and the medium 2 is placed on the agent holder 4.

Next, the inner container 5N of the second container 1N accommodating the desiccant 61 inside with the cap section 11N being detached is disposed in the container containing section 52 of the container body 5M of the first container 1M (see FIGS. 14 (*a*) and (*b*)). By disposing the inner container 5N in the container containing section 52, the medium 2 is placed between the containing section 6 of the desiccant 61 and the agent holder 4.

Subsequently, the cap section 11M of the first container 1M is fitted to the container body 5M, and thereby the medium 2 closely contacts the agent holder 4. More specifically, when the cap section 11M is fitted to the container body 5M, the top surface section 31*m* of the cap section 11M abuts on an upper end section 60*a* of the desiccant-containing body 60 of the inner container 5N, and the inner container 5N is pushed down. When the inner container 5N is pushed down, the medium 2 is pressed against the agent holder 4 by a bottom portion of the desiccant-containing body 60, and the medium 2 closely contacts the agent holder 4. In the fifth embodiment, from the viewpoint of reliably bringing the medium 2 into close contact with the agent holder 4 when the cap section 11M of the first container 1M is fitted to the container body 5M, a distance L1 (see FIG. 12 (*a*)) from a back surface of the top surface section 31*m* to a top surface of a bottom portion of the container body 5M in the state in which the cap section 11M is fitted to the container body 5M is smaller than a total value of a height L2 of the inner container 5N (see FIG. 13), and a thickness L3 (see FIG. 12 (*a*)) of the agent holder 4 in which no outer force is applied.

Further, when the cap section 11M of the first container 1M is fitted to the container body 5M, the seal member 41 of the cap section 11M abuts on an upper end section of the container body 5M, and the space in the container body 5M is hermetically closed.

Further, in the fifth embodiment, a communicating passage that causes the containing section 6 of the desiccant 61 and the containing section 51 of the agent holder 4 to communicate with each other is formed, in the state in which the inner container 5N is accommodated in the container body 5M and the cap section 11M is fitted to the container body 5M. Hereinafter this point is described in detail.

In a storage container 1G in which an inside is hermetically closed, a gap is formed between the upper end section 60*a* of the desiccant-containing body 60 and the top surface section 31*m* of the cap section 11M. More specifically, in the storage container 1G, as shown in FIG. 14 (*b*), the convex stripe portion 33 of the top surface section 31*m* of the cap section 11M abuts on the upper end section 60*a* of the desiccant-containing body 60, and a gap is formed between a part other than the convex stripe portion 33 in the back surface of the top surface section 31*m* and the upper end section 60*a* of the desiccant-containing body 60. The gap configures a part of the communicating passage that causes the containing section 6 of the desiccant 61 and the containing section 51 of the agent holder 4 to communicate with each other.

Further, in the storage container 1G, as shown in FIG. 14 (*b*), a gap is formed between a lower end portion 71*b* of the container circumferential wall portion 71 of the inner container 5N, and a connection portion 56 of the container body 5M. The gap also configures a part of the communicating passage that causes the containing section 6 of the desiccant 61 and the containing section of the agent holder 4 to communicate with each other.

In this way, in the storage container 1G in which the inside is hermetically closed, the containing section 6 of the desiccant 61 and the containing section 51 of the agent holder 4 communicate with each other via the gap between the upper end section 60*a* of the desiccant-containing body 60 and the top surface section 31*m* of the cap section 11M, and the gap between the lower end portion 71*b* of the container circumferential wall portion 71 of the inner container 5N and the connection portion 56 of the container body 5M. Accordingly, in the storage container 1G in which the inside is hermetically closed, the desiccant 61 absorbs humidity released from the degradation inhibitor 3 via these gaps without directly contacting the agent holder 4. In this way, according to the specimen-preserving implement 1K of the fifth embodiment, similar effects to the effects of the specimen-preserving implements of the first to the fourth embodiments are exhibited.

A method for providing the specimen-preserving implement 1K of the fifth embodiment to the user or the like is described by showing a preferable example.

First, on a side of a provider who provides the specimen-preserving implement 1K to a user or the like, the agent holder 4 and the desiccant 61 are accommodated in the first container 1M and the second container 1N, respectively. Specifically, after the agent holder 4 impregnated with the liquid degradation inhibitor is accommodated in the holder containing section 51 of the container body 5M, the cap section 11M is fitted to the one end opening of the container body 5M to form the first container 1M in which the agent holder 4 is accommodated. Further, after the desiccant 61 is accommodated in the inner container 5N, the cap section 11N is fitted to the opening of the inner container 5N to form the second container 1N in which the desiccant 61 is accommodated.

Subsequently, the first container 1M and the second container 1N that are formed in this way are brought into a state in which the first container 1M and the second container 1N are packaged in a packaging container together with the medium 2A that can hold a specimen and are sent to the user or the like, and thereby the specimen-preserving implement 1K is provided.

The specimen-preserving implement 1K of the fifth embodiment may not have the cap section 11N of the second container 1N, but preferably includes a pre-use sealing member for sealing an opening of the containing section 6 of the desiccant 61 in the inner container 5N. In the fifth embodiment, the pre-use sealing member is the cap section 11N of the second container 1N. When the specimen-preserving implement 1K has the pre-use sealing member, the inner container 5N is preferably provided to a user in a state in which the opening of the containing section 6 of the desiccant 61 is sealed with the pre-use sealing member, in other words, in the state in which the cap section 11N is fitted to the inner container 5N. By providing the inner container 5N in the state in which the opening of the containing section 6 of the desiccant 61 is sealed with the pre-use sealing member, it is possible to prevent foreign substances other than the desiccant 61 from entering into the containing section 6 of the desiccant 61, and the desiccant 61 from coming out of the containing section 6 of the desiccant 61. As the pre-use sealing member, a shielding film such as Parafilm (trademark) or the like can also be used.

Figure 15:
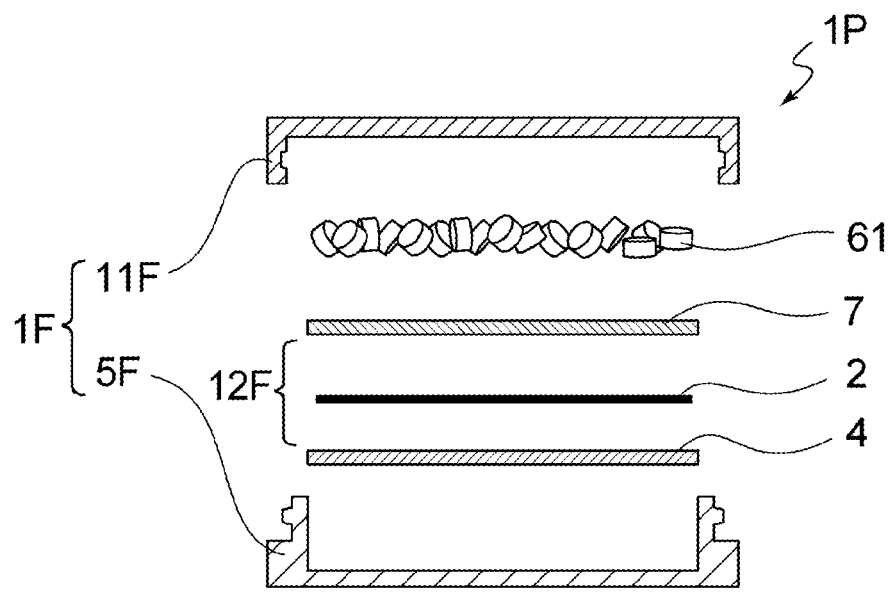
FIG. 15 (*a*) and FIG. 15 (*b*) are views showing the specimen-preserving implement according to the fifth embodiment of the present invention, FIG. 15 (*a*) is an exploded view, and FIG. 15 (*b*) is a sectional view showing a specimen storage state.
Figure 15:
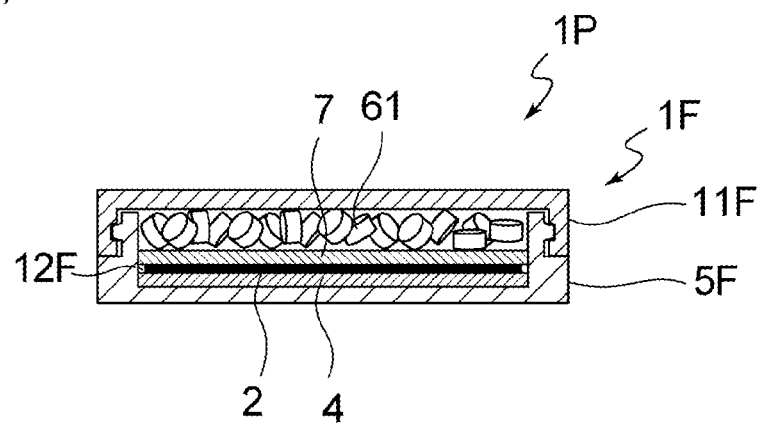

FIG. 15 (*a*) and FIG. 15 (*b*) are views showing a specimen-preserving implement 1P of a sixth embodiment of the present invention. The specimen-preserving implement 1P of the sixth embodiment includes a container 1F having a cap section 11F, and a container body 5F to which the cap section 11F is detachably and attachably fitted. In a state of the specimen-preserving implement being provided to a user, in the container 1F, only an agent holder 4 impregnated with a liquid degradation inhibitor 3 is placed inside.

Further, the specimen-preserving implement 1P of the sixth embodiment has a sheet-like medium 2, a disk-shaped contact-suppressing member 7, and a desiccant 61 that are accommodated in a bag container or the like separate from the container 1F and provided. The contact-suppressing member 7 can make humidity released from the agent holder 4 or the degradation inhibitor that transfers to the medium 2 from the agent holder 4 pass through and allow the desiccant 61 to absorb the humidity, while can separate the desiccant 61 and the agent holder 4 from each other so that the desiccant 61 and the agent holder 4 do not directly contact each other, similarly to the contact-suppressing member 7 in the first embodiment.

When using the specimen-preserving implement 1P of the sixth embodiment, the cap section 11F is detached from the container body 5F, and the disk-shaped agent holder 4 that is placed in the container body 5F, is impregnated with the liquid degradation inhibitor in advance, and has a predetermined thickness is exposed. The agent holder 4 is formed of a member such as sponge having an elastic restoring force to compression. Subsequently, on the agent holder 4, a medium 2 after holding a specimen is placed on a sheet-like medium 2A'. The medium 2 may be placed on the agent holder 4 as one sheet in a developed state, or may be placed on the agent holder 4 by being folded up one or a plurality times to be brought into a compact state. Next, the contact-suppressing member 7 and the desiccant 61 are sequentially placed on the medium 2, and thereafter, the cap section 11F is fitted on the container body 5F.

According to the specimen-preserving implement 1P of the sixth embodiment, the medium 2 can be placed in a medium-containing section 12F located on the agent holder 4 in a state in which the agent holder 4 is impregnated with the liquid degradation inhibitor 3, and thereby, the degradation inhibitor 3 transfers to the medium 2. The medium 2 placed in the medium-containing section 12F is preferably closely contacted to the agent holder 4 by the contact-suppressing member 7 or another member, and is more preferably pressed against the agent holder 4. In order to be closely contacted to or pressed against the agent holder 4, it is possible to adopt any method such as making a total thickness of the members placed between the container body 5F and the cap section 11F larger than a thickness between the container body 5F and the cap section 11F. Further, as shown in FIG. 15 (b), in the container 1F in which the inside is hermetically closed, the desiccant 61 absorbs the humidity released from the degradation inhibitor 3 via the contact-suppressing member 7 without directly contacting the agent holder 4. In this way, according to the specimen-preserving implement 1P of the sixth embodiment, similar effects to the effects of the specimen-preserving implements of the first to the fifth embodiments are exhibited.

Figure 16:
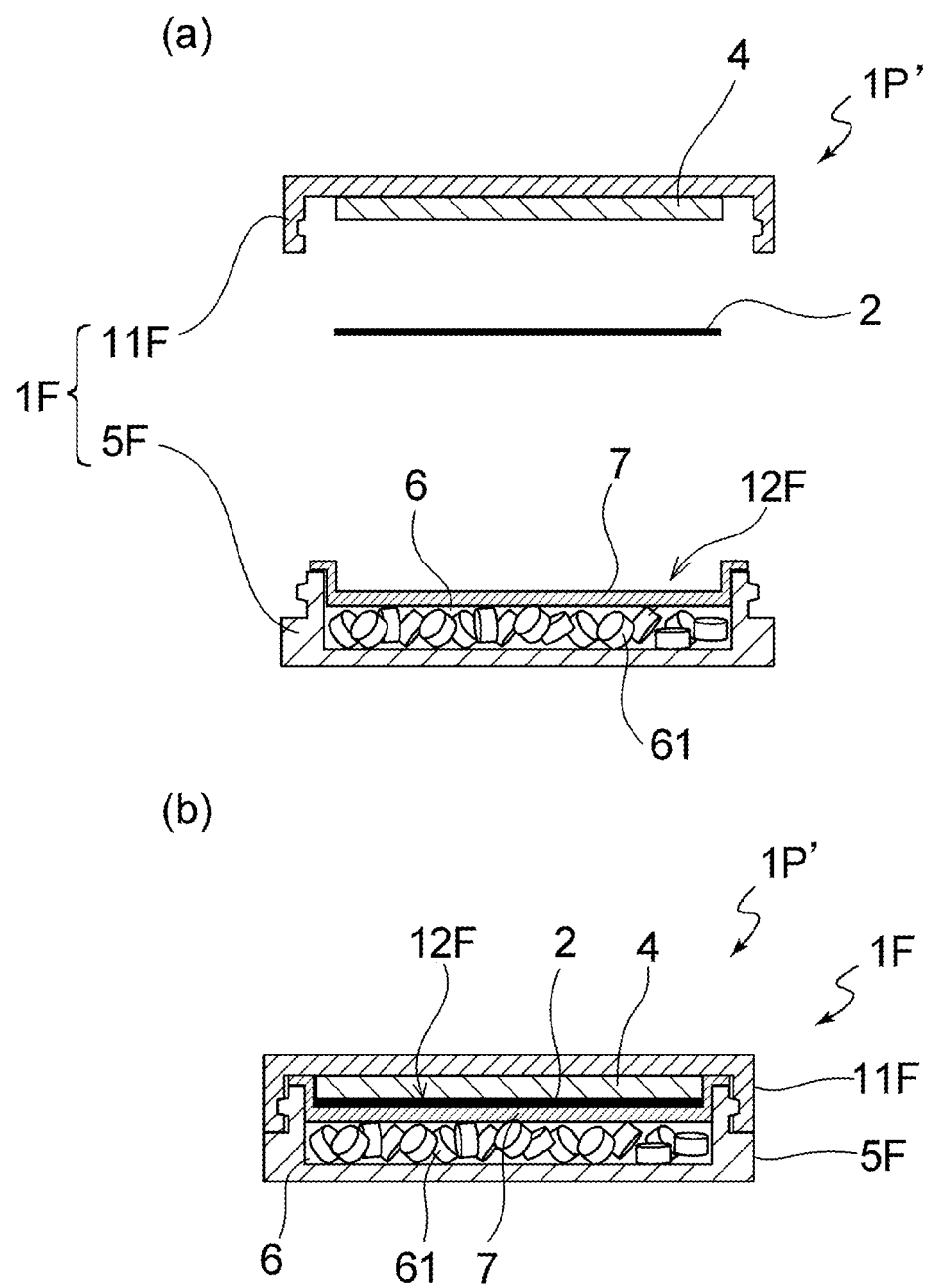
FIG. 16 (*a*) and FIG. 16 (*b*) are views showing a specimen-preserving implement according to a sixth embodiment of the present invention, FIG. 16 (*a*) is a view in which a container body and a cap section are separated, and FIG. 16 (*b*) is a sectional view showing a specimen storage state.

A specimen-preserving implement 1P' of a seventh embodiment is shown in FIG. 16 (a) and FIG. 16 (b). A difference lies in that in the specimen-preserving implement 1P of the sixth embodiment, the agent holder 4 impregnated with the liquid degradation inhibitor 3 is placed on the container body 5F side, of the cap section 11F and the container body 5F in the container 1F before use, whereas in the specimen-preserving implement 1P' of the seventh embodiment, as shown in FIG. 16 (a) and FIG. 16 (b), an agent holder 4 impregnated with a liquid degradation inhibitor 3 is fixed to a cap section 11F side in a container 1F before use.

In the specimen-preserving implement 1P' of the seventh embodiment, the contact-suppressing member 7 is fixed by being fitted to an opening of a container body 5F in the container 1F before use, and a containing section 6 of a desiccant is formed between the container body 5F and the contact-suppressing member 7. In the seventh embodiment, a space between the contact-suppressing member 7 and the agent holder 4 is a medium-containing section 2F. When a medium 2 is placed between the agent holder 4 impregnated with the liquid degradation inhibitor 3 and the contact-suppressing member 7 and a cap section 11F is closed, the agent holder 4 is brought into close contact with, preferably, pressure contact with the medium 2, and the degradation inhibitor 3 in the agent holder 4 favorably transfers to the medium 2.

If the desiccant 61 is accommodated in advance in the containing section 6 of the desiccant formed in the container body 5F of the container 1F, there is an advantage of being able to prevent the desiccant 61 from jumping outside when removing the cap section 11F at the time of use, or the like. The contact-suppressing member 7 is formed of a synthetic resin, for example, and has a plurality of ventilation holes formed therein. As the contact-suppressing member 7, a cotton-like, sheet-like, or plate-like member or the like can be used. The ventilation holes of the contact-suppressing member 7 are preferably closed with a seal member or the like before the medium 2 is placed.

According to the specimen-preserving implement 1 P' of the seventh embodiment, similar effects to the effects of the specimen-preserving implements of the first to the fifth embodiments or the sixth embodiment are exhibited.

The present invention is described thus far based on the preferable embodiments, but the present invention is properly changeable without being limited to the above-described embodiments, the configurations of the aforementioned respective embodiments may be properly combined.

For example, in the specimen-preserving implement 1" of the fourth embodiment, the single container 1E includes the desiccant-containing body 60, and the agent holder 4 in the state of being impregnated with the liquid degradation inhibitor, but instead of this, the specimen-preserving implement may have a first container provided with the desiccant-containing body 60 equipped with a cap section, and a second container in which the agent holder 4 in a state of being impregnated with a liquid degradation inhibitor is placed inside of a container body, and when the cap section detached from the container body of the first container is fitted to the container body of the second container, the desiccant-containing body provided in the cap section of the first container can be configured to push the medium 2 holding a specimen into the container body of the second container.

Further, in the specimen-preserving implement 1K of the fifth embodiment, the first container 1M and the second container 1N, and the medium 2A capable of holding a specimen may be provided separately, or the first container 1M, the second container 1N, and the medium 2A may be provided separately.

Further, the specimen-preserving implement 1K may be provided to a user or the like without accommodating the agent holder 4 and the desiccant 61 respectively in the first container 1M and the second container 1N. More specifically, the first container 1M and the second container 1N that accommodate nothing inside, the agent holder 4, the desiccant 61, and the medium 2A may be brought into a state of being separately wrapped respectively, and these may be packaged in a packaging container and sent to a user or the like.

In the second to the seventh embodiments, the modes of the degradation inhibitor being held by the agent holder in advance are described, but in each of these modes, the liquid degradation inhibitor can be put into another container such as a bag or a tube that are separated from the container including the agent holder, and can be given to the agent holder directly before use.

Further, a cap section that is fittable to the container body 5B of the second container 1B may be formed by integral molding or the like at an outside of the bottom portion of the container body 5A or 5A' of the first container 1A or 1A' in the first or the second embodiment, and the cap section may be used as the cap section 11B that closes the opening of the second container 1B before use. Further, the opening of the container body of the second container 1B may be closed with a shielding film such as Parafilm (trademark).

INDUSTRIAL APPLICABILITY

According to the specimen-preserving implement of the present invention, it is possible to contacting the liquid degradation inhibitor to the specimen efficiently while preventing contact of the liquid degradation inhibitor and a body by impregnating the agent holder with the liquid degradation inhibitor to contact the agent holder to the specimen, and it is possible to effectively inhibit leak of the liquid degradation inhibitor and degradation of the component to be tested in the specimen by reducing the moisture in the liquid degradation inhibitor after accommodation of the specimen.

The invention claimed is:

1. A specimen-preserving implement comprising:
   a medium-containing section capable of accommodating a medium holding a specimen;
   a degradation inhibitor in liquid form that inhibits degradation of a sample to be tested contained in the specimen;
   an agent holder capable of being impregnated with the degradation inhibitor; and
   a receptacle of a desiccant,
   wherein the degradation inhibitor transfers to the medium by placing the medium in the medium-containing section in a state in which the agent holder is impregnated with the degradation inhibitor, and the desiccant is enabled to absorb humidity released from the degradation inhibitor without directly contacting the agent holder in a state in which the medium is accommodated in the medium-containing section.

2. The specimen-preserving implement according to claim 1, further comprising:
   a container including a cap and a container body to which the cap is fitted; and
   an inner container configured to be accommodated in the container,
   wherein the agent holder is placed in the container body,
   wherein the inner container includes a desiccant-containing body including the receptacle of the desiccant,
   wherein the medium-containing section is formed between the desiccant-containing body and the agent holder in a state in which the inner container is accommodated in the container body and the cap is fitted to the container body, and
   wherein the medium contacts the agent holder by detaching the cap from the container body, placing the medium between the receptacle of the desiccant and the agent holder, and thereafter fitting the cap to the container body.

3. The specimen-preserving implement according to claim 2,
   wherein in the state in which the inner container is accommodated in the container body and the cap is fitted to the container body, a gap is formed between an upper end section of the desiccant-containing body and a top surface section of the cap, and the gap configures a part of a communicating passage that causes the receptacle of the desiccant and a receptacle of the agent holder to communicate with each other.

4. The specimen-preserving implement according to claim 2,
   wherein the cap has a seal member on a back surface side of the top surface section of the cap, and
   in a state in which the cap is fitted to the container body, the seal member abuts on an upper end section of the container body, and a space in the container body is hermetically closed.

5. The specimen-preserving implement according to claim 2, further comprising:
   a pre-use sealing member that seals an opening of the receptacle of the desiccant of the inner container,
   wherein the inner container is provided to a user in a state in which the opening is sealed with the pre-use sealing member, and
   wherein the inner container is accommodated in the container body and the cap is fitted to the container body, in a state in which the pre-use sealing member is detached.

6. The specimen-preserving implement according to claim 1, further comprising:
   a first container including a cap including the agent holder and a container body to which the cap is fitted, in which the agent holder includes the medium-containing section; and
   a second container including a container body to which the cap is capable of being fitted, and including the receptacle of the desiccant inside.

7. The specimen-preserving implement according to claim 6,
   wherein after the medium holding the specimen is held in the medium-containing section of the cap detached from the container body of the first container, the cap is capable of being fitted to the container body of the second container.

8. The specimen-preserving implement according to claim 6,
   wherein the first container includes a storage of the degradation inhibitor and the agent holder, and the storage can maintain the degradation inhibitor and the agent holder in a state of being separated from each other until a predetermined operation is performed.

9. The specimen-preserving implement according to claim 1, wherein the agent holder comprises a medium-inserted portion, as the medium-containing section, in which the medium is inserted and held.

10. The specimen-preserving implement according to claim 9, further comprising:
    a pair of outside support portions that cover an outer surface side of the agent holder in each of both sides of the medium-inserted portion,
    wherein by increasing or decreasing a pressing force with the pair of outside support portions between fingers, pressure that presses the agent holder against the medium inserted into the medium-inserted portion can be increased or decreased.

11. The specimen-preserving implement according to claim 1, further comprising:
    a container including a cap; and
    a container body to which the cap is fitted,
    wherein a desiccant-containing body including the receptacle of the desiccant inside is attached to the cap,
    wherein the agent holder is placed in the container body, and
    wherein a space between the desiccant-containing body and the agent holder in a state in which the cap is fitted to the container body is the medium-containing section, and the medium is brought into contact with the agent holder by detaching the cap from the container body, placing the medium adjacently to the desiccant-containing body, and thereafter fitting the cap to the container body.

12. The specimen-preserving implement according to claim 9, further comprising:
    a medium capable of holding a specimen.

13. The specimen-preserving implement according to claim 11, wherein the desiccant-containing body is formed of an agent-impermeable material that is impermeable to the degradation inhibitor, and has a ventilation hole that causes an inside and outside of the receptacle of the desiccant to communicate with each other formed in a site that does not contact the medium and the agent holder.

14. The specimen-preserving implement according to claim 1, wherein the specimen is a biological specimen derived from an animal, and the sample to be tested is a nucleic acid.

15. The specimen-preserving implement according to claim 14, wherein the sample to be tested is RNA.

16. The specimen-preserving implement according to claim 1, wherein the medium is sheet-like.

17. A specimen-preserving implement comprising:
a container including a cap and a container body to which the cap is fitted; and
a desiccant-containing body configured to be accommodated in the container,
wherein an agent holder capable of being impregnated with a degradation inhibitor in liquid form that inhibits degradation of a sample to be tested contained in a specimen is placed in the container body, and the desiccant-containing body includes a receptacle of a desiccant, and
wherein a medium-containing section capable of accommodating a medium holding the specimen is formed between the desiccant-containing body and the agent holder for the medium to contact with the agent holder in a state in which the desiccant-containing body is accommodated in the container body and the cap is fitted to the container body.

18. A specimen-preserving implement comprising:
a container including a cap and a container body to which the cap is fitted; and
an inner container configured to be accommodated in the container,
wherein an agent holder capable of being impregnated with a degradation inhibitor in liquid form that inhibits degradation of a sample to be tested contained in a specimen is placed in the container body, and the inner container includes a desiccant-containing body including a receptacle of a desiccant,
wherein a medium-containing section capable of accommodating a medium holding the specimen is formed between the desiccant-containing body and the agent holder in a state in which the inner container is accommodated in the container body and the cap is fitted to the container body,
wherein a distance from a back surface of a top surface section of the cap to a top surface of a bottom portion of the container body is smaller than a total value of a height of the inner container and a thickness of the agent holder in which no outer force is applied.

* * * * *